(12) United States Patent
Zimmermann et al.

(10) Patent No.: US 10,017,725 B2
(45) Date of Patent: Jul. 10, 2018

(54) CULTURE VESSEL AND METHOD FOR CULTURING BIOLOGICAL CELLS IN HANGING DROPS

(71) Applicant: Fraunhofer-Gesellschaft zur Foerderung der angewandten Forschung e.V., Munich (DE)

(72) Inventors: Heiko Zimmermann, Waldbrunn (DE); Guenter R. Fuhr, Berlin (DE); Julia Neubauer, St. Ingbert (DE)

(73) Assignee: FRAUNHOFER-GESELLSCHAFT ZUR FOERDERUNG DER ANGEWANDTEN FORSCHUNG E.V., Munich (DE)

( * ) Notice: Subject to any disclaimer, the term of this patent is extended or adjusted under 35 U.S.C. 154(b) by 381 days.

(21) Appl. No.: 14/894,044

(22) PCT Filed: Jun. 25, 2014

(86) PCT No.: PCT/EP2014/001717
§ 371 (c)(1),
(2) Date: Nov. 25, 2015

(87) PCT Pub. No.: WO2015/003775
PCT Pub. Date: Jan. 15, 2015

(65) Prior Publication Data
US 2016/0108352 A1    Apr. 21, 2016

(30) Foreign Application Priority Data

Jul. 10, 2013   (DE) .................. 10 2013 011 534

(51) Int. Cl.
*C12M 1/12* (2006.01)
*C12M 1/00* (2006.01)
*C12M 1/06* (2006.01)

(52) U.S. Cl.
CPC ............ *C12M 25/01* (2013.01); *C12M 23/22* (2013.01); *C12M 23/26* (2013.01); *C12M 23/34* (2013.01); *C12M 25/06* (2013.01)

(58) Field of Classification Search
CPC ...... C12M 23/26; C12M 23/34; C12M 25/01; C12M 23/22; C12M 25/06
See application file for complete search history.

(56) References Cited

U.S. PATENT DOCUMENTS 7,316,805 B1    1/2008  Viola et al.
8,906,685 B2   12/2014  Takayama et al.
(Continued)

FOREIGN PATENT DOCUMENTS

DE    19949735 A1   5/2001
JP    2001026797 A  1/2001
(Continued)

OTHER PUBLICATIONS

English language abstract for WO 01/26797 A2 corresponding to DE 199 49 735 A1 (2001).
(Continued)

*Primary Examiner* — Gautam Prakash
(74) *Attorney, Agent, or Firm* — Caesar Rivise, PC

(57) ABSTRACT

A culture vessel (100), which is designed for culturing biological cells (1) in hanging drops (2), comprises a vessel wall (10), which has a cover portion (11) and a floor portion (12), wherein the cover portion (11) is designed to provide a culturing surface (13), and the floor portion (12) is designed to receive a liquid (3), the vessel wall (10) encloses an interior (20) of the culture vessel on all sides, the culturing surface (13) has holding elements (14), which are designed to position the drops (2), wherein the culturing surface (13) can receive the drops (2) hanging freely in the interior (20), and the vessel wall (10) is movable such that (Continued)

the holding elements (14) can be wetted with the liquid (3) from the floor portion (12). A method for culturing biological cells (1) in hanging drops (2) in the culture vessel (100) is also described.

23 Claims, 10 Drawing Sheets

(56) References Cited

U.S. PATENT DOCUMENTS

| | | |
|---|---|---|
| 9,126,199 B2 | 9/2015 | Moritz et al. |
| 2007/0184551 A1 | 8/2007 | Viola et al. |
| 2008/0111442 A1 | 5/2008 | Tussing |
| 2010/0112684 A1 | 5/2010 | Lee et al. |
| 2011/0306122 A1 | 12/2011 | Moritz et al. |
| 2013/0040855 A1 | 2/2013 | Takayama et al. |
| 2014/0179561 A1 | 6/2014 | Takayama et al. |

FOREIGN PATENT DOCUMENTS

| | | |
|---|---|---|
| JP | 2002536255 A | 10/2002 |
| JP | 2008125347 A | 5/2008 |
| JP | 2012014047 A | 1/2012 |
| JP | 2012502636 A | 2/2012 |
| JP | 2013517809 A | 5/2013 |
| KR | 100836827 B1 | 6/2008 |
| WO | 0047323 A1 | 8/2000 |
| WO | 2008125347 A1 | 10/2008 |
| WO | 2011094572 A2 | 8/2011 |
| WO | 2012014047 A1 | 2/2012 |

OTHER PUBLICATIONS

International Search Report for PCT/EP2014/001717 dated Oct. 7, 2014.

Japanese Patent Office Communication from corresponding JP 2016-524699 dated Jan. 10, 2018.

CULTURE VESSEL AND METHOD FOR CULTURING BIOLOGICAL CELLS IN HANGING DROPS

BACKGROUND OF THE INVENTION

The invention relates to a culture vessel which is adapted for culturing biological cells in hanging droplets, in particular a culture vessel in the inner space of which a culturing area is provided for receiving the hanging droplets. The invention also relates to a method for culturing biological cells in hanging droplets. Uses of the invention lie in the culturing of biological cells, in particular stem cells.

The cultivation (multiplication and/or differentiation) of biological cells in hanging droplets is a widely used culturing method. The biological cells can be cultured in the hanging droplets, wherein contact with solid substrate surfaces is avoided and a geometric arrangement of the cells similar to the arrangement of cells during their multiplication and differentiation in nature is realized. For the formation of the hanging droplets and their loading with the cells, the following techniques are conventionally known.

In a method which is typically performed manually, a flat bowl with a planar bottom, for example, the cover of a Petri dish is used. Initially, the cover is arranged on a support in such a way that an inner surface of the cover is exposed. Droplets of a cell suspension are placed on the surface with a pipette and subsequently, the cover is turned over by means of a pivoting movement such that the surface loaded with the droplets faces downwardly. The pivoting movement must take place so rapidly that the droplets do not run but remain in their places and, as a result, hang free on the downwardly facing inner surface of the cover after the pivoting. For the culturing, the cover is arranged, for protection against drying out, on the associated bottom of the Petri dish filled with an aqueous solution. This technique has the advantage of being simple to perform. However, disadvantages arise from the necessarily rapid and sudden pivot movement of the cover, which requires a high degree of skill from the user and permits automation to only a limited degree. Furthermore, undesired shear forces can arise in the droplets and these can have disadvantageous effects on sensitive cells, particularly stem cells.

Alternatively, hanging droplets can be generated on cell culture plates with holes which are surrounded at an underside of the plates by holding rings for holding the droplets by means of capillary forces. The formation of the droplets and their loading on one of the holding rings takes place in that the cell suspension is fed in through the associated hole in the plate and is hung as droplet on the holding ring (see also WO 2008/125347). The cell culture plate favors automation of the culturing method and the avoidance of the aforementioned shear forces. It is disadvantageous, however, that this technique demands special measures for preventing undesirable influences from the surroundings and mutual contamination of adjacent droplets.

It is an objective of the invention to provide an improved culture vessel which is configured for culturing biological cells in hanging droplets and is able to avoid disadvantages of conventional techniques. The culture vessel should enable, in particular, a gentle formation of the hanging droplets, offer protection of the hanging droplets and/or be automatable. It is a further objective of the invention to provide an improved method for culturing biological cells in hanging droplets, with which the disadvantages of conventional techniques are avoided. The method should, in particular, simplify the formation of the hanging droplets, wherein undesired shear forces can be minimized or excluded and/or enable the provision of pre-determined, reproducible culturing conditions.

These objectives are achieved by means of a culture vessel of the invention and a culturing method using the culture vessel, of the invention.

SUMMARY OF THE INVENTION

According to a first aspect of the invention, the aforementioned object is achieved with a culture vessel which is configured for culturing biological cells in hanging droplets and has a vessel wall with a cover section and a bottom section. The cover section is configured for the provision of a culturing area for receiving the hanging droplets. The culturing area has a surface which, when the culture vessel is used for culturing biological cells, faces vertically downwardly, i.e. in the direction of gravity. The bottom section is configured for receiving a liquid. The bottom section forms a reservoir for the liquid which comprises, for example, an aqueous medium with biological cells, in particular a cell suspension in a culture medium. The cover and bottom sections have a laminar, preferably planar or at least partially curved, extent, and in use during the culturing, preferably extend in a horizontal direction and/or with a substantially constant spacing.

The vessel wall is formed such that an inner space of the culture vessel is enclosed by the cover section and the bottom section on all sides. The inner space is delimited from the surroundings by the vessel wall. Advantageously, this enables a local setting of culturing conditions such as, for example, the provision of a gaseous culture medium, a specified air humidity and/or a specified temperature in the culture vessel.

According to the invention, the culturing area is provided with holding elements which are configured for positioning the hanging droplets. The holding elements are formed such that when they are wetted with the culture liquid, a collection of liquid and a formation of the hanging droplets are supported on the holding elements. The inner space is formed such that the culturing area can receive the droplets freely hanging. Preferably, the cover section and the bottom section have a mutual working distance in which the droplets can hang free at the culturing area in the inner space of the culture vessel without touching liquid on the bottom section.

Furthermore, according to the invention, the vessel wall of the culture vessel is configured movable so that the holding elements can be wetted with the liquid from the bottom section. The movability of the vessel wall means that the whole culture vessel can be moved, for example, with a pivoting device, or that parts of the vessel wall can be moved relative to one another. The movability of the vessel wall also means that the liquid from the bottom section temporarily comes into contact with the cover section. Since the culture vessel according to the invention has a closed inner space, during a movement of the culture vessel, a movement of the liquid can take place without it emerging into the surroundings. Sudden movements of the culture vessel are avoidable, unlike the above mentioned manual technique. Any undesirable shear forces in the liquid can be minimized or excluded.

According to a second aspect of the invention, the aforementioned objective is achieved by means of a method for culturing biological cells in hanging droplets wherein the culture vessel according to the first aspect of the invention is used. A liquid, particularly a suspension, which contains the biological cells in a liquid medium is provided at the bottom section of the culture vessel. The vessel wall of the culture vessel is moved such that the culturing area is wetted by the suspension including the biological cells. Subsequently, a return of the vessel wall takes place wherein the culturing area is separated from the suspension on the bottom section and droplets of the suspension with the cells are gathered on the holding elements. Subsequently, the culturing (multiplication and/or differentiation) of the biological cells in the hanging droplets takes place, wherein, for example, cell aggregates and/or differentiated cells are formed.

The invention offers a series of advantages in comparison with the conventional techniques. The mobility of the closed vessel wall enables loading of the culturing area without any sudden pivoting of the culture vessel. The wetting of the culturing area can take place with a minimally moving or static cell suspension. In the formation of the hanging droplets, shear forces can be eliminated or minimized to a non-damaging extent. The culture vessel according to the invention enables a gentle transfer of the cells from the suspended state to the hanging droplet. A further advantage of the culture vessel according to the invention results therefrom that the vessel wall forms the closed inner space. Influences from the surroundings are minimized. Adjustment of the culturing conditions in the inner space is simplified. Undesirable contaminations are eliminated. Finally, the culture vessel according to the invention enables automation of the culturing of biological cells in hanging droplets. The entire process of culturing, starting with the provision of the cell suspension and the formation of the hanging droplets and further with the multiplication and/or differentiation of the cells in the hanging droplets, can be automated. Manual actuation of the culture vessel for loading the culturing area is possible, but is not dependent on the skill of the operator and is therefore readily automatable.

The culturing area of the culture vessel according to the invention is provided with holding elements which determine the positions of the hanging droplets. According to a preferred embodiment of the invention, the holding elements comprise hydrophilic surface regions (hydrophilic islands, hydrophilic spots) of the culturing area which are separated from one another by hydrophobic surface regions. The hydrophilic surface regions advantageously enable reliable collection of the droplets of aqueous medium. The size of the droplets can be influenced by the size of the hydrophilic surface regions.

Advantageously, various possibilities exist for the design of the holding elements. If, for example, the culturing area is formed by a surface of a film, the hydrophilic and/or the hydrophobic surface regions are provided by functionalizing the film surface. Alternatively or additionally, according to a further variant, the holding elements can comprise hydrophilic step elements, in particular local depressions or projections of the culturing area on which the effect of capillary forces is greater than in unstructured surface regions of the culturing area. If the culturing area is formed, for example, by the surface of a plastics panel or film, the hydrophilic step elements can be formed by ring-shaped, square or cylindrical projections with typical dimensions (cross-section, height) in the sub-mm range. Particularly preferably, the hydrophilic step elements comprise circumferential projections, e.g. in the form of rings. Circumferential, e.g. ring-shaped projections can fulfil a double function: during the culturing of cells or cell aggregates in the hanging droplets, the projections form a delimitation relative to adjacent hanging droplets, and during optionally provided further culturing in the adherent state, said projections form a receptacle for a culture medium.

Preferably the holding elements, in particular the hydrophilic surface regions are arranged in a regular pattern, e.g. a matrix arrangement with straight rows and columns of the holding elements. Advantageously, the identification of samples in individual hanging droplets and the automation of the culturing according to the invention in hanging droplets are thereby simplified.

Advantageously, the movement of the vessel wall for wetting the culturing area can take place without the whole culture vessel being pivoted. According to a preferred embodiment of the invention, the culture vessel has a deformable vessel wall. The cover section and the bottom section are movable relative to one another. During a deformation of the vessel wall (compression of the culture vessel) the spacing of the cover section and the bottom section can be reduced so that the culturing area with the holding elements can be moved close to the bottom section. Advantageously, the deformability of the vessel wall enables the culturing area and the bottom section to be moved toward one another such that the holding elements come into contact with the liquid which is accommodated on the bottom section. The vessel wall is deformable such that the culturing area can be wetted with the liquid on the bottom section, e.g. immersed in the liquid.

In this embodiment of the invention, the formation of the hanging droplets comprises firstly a compression of the culture vessel in order to wet the holding elements with the liquid. Subsequently, a restoration of the vessel wall takes place, wherein the spacing of the cover section and of the bottom section increases again until a desired working distance between them for receiving the hanging droplets is achieved. During the restoring of the vessel wall, the culturing area is separated from the suspension on the bottom section, wherein suspension with the cells gathers on the holding elements so that hanging droplets are formed on the holding elements.

The vessel wall of the culture vessel according to the invention can be made of a plurality of materials for providing the cover and bottom sections or alternatively can be made in one piece of a single material. There are different possibilities for the material selection in order to provide the desired deformability of the vessel wall. According to a preferred embodiment of the invention, the vessel wall can be manufactured from a flexible film material. In this case, the culture vessel forms a flexible bag in the form of a flattened cushion which, when the culture vessel is used, extends substantially in the horizontal direction. The cover and bottom areas of the culture vessel are provided by the main areas of the bag. The spacing between the culturing area and the bottom section, in particular a clear width of the inner space in the culture vessel made of the flexible film material can be adjusted under the effect of an internal pressure in the culture vessel and/or using a foldable inner carrier. The internal pressure can be adjusted by a pump device or by reducing the volume of the inner space, e.g. at a rolling-up portion or a squeezing portion of the culture vessel. The foldable inner carrier can comprise a collapsible frame in the inner space of the culture vessel.

According to an alternative embodiment of the invention, the vessel wall is manufactured at least partially from an elastically deformable material. In this case, the working distance between the cover and bottom sections can be adjustable under the effect of an internal elastic restoring force of the elastically deformable material. Preferably, the elastically deformable material is provided in the cover section and/or in the bottom section in edge regions in which the connection to the bottom section or the cover section is formed. The elastically deformable material preferably forms a side section by means of which the cover and bottom sections are connected to one another at the side, i.e. laterally in relation to the culturing area and the cell suspension at the bottom section.

According to a preferred embodiment of the invention, the vessel wall can be composed from a flexible film material and an elastically deformable material. For example, the flexible film material can be provided along the lateral extent of the cover and bottom sections, whilst the elastically deformable material is provided in the edge regions between the cover and bottom sections, particularly forming the side section. Furthermore, the vessel wall can be manufactured entirely or partially from an elastic, flexible film material.

According to a further variant of the invention, the vessel wall can be manufactured partially from a rigid plate-shaped wall material. The plate-shaped wall material can form, for example, the cover and/or bottom sections along their lateral extent, whilst edge regions of the cover and bottom sections are formed over the side section from the elastically deformable material and/or the flexible film material.

Preferably, the bottom section is formed such that the liquid can entirely cover the bottom section in the culture vessel. By this means, in the compressed state of the culture vessel, the whole culturing area can be wetted. The effectiveness of the formation of hanging droplets is improved. According to a modified embodiment of the invention, the bottom section can have a bottom area opposite to the culturing area in the inner space of the culture vessel, said bottom area being configured for a locally selective provision of the liquid on hydrophilic surface regions which are separated from one another by means of hydrophobic surface regions. The hydrophilic surface regions of the bottom area are positioned with the same geometric arrangement as the holding elements of the culturing area. The positions of the hydrophilic surface regions of the bottom area match the positions of the holding elements of the culturing area. Advantageously as a result, the liquid consumption on formation of the hanging droplets can be significantly reduced. In the bottom section, the liquid, particularly the cell suspension is provided only in the hydrophilic surface regions and thus at the positions where hanging droplets can be formed during the approach of the culturing area.

Preferably, the culturing area of the culture vessel is formed directly by an inner surface of the cover section. Advantageously, in this case, the hanging droplets can be formed directly on the inner side of the vessel wall. An observation and possibly a manipulation of the droplets and the construction of the culture vessel are simplified. Alternatively, the culturing area can be provided on another interior surface in the inner space of the culture vessel.

According to a further advantageous embodiment of the invention, the culture vessel can have at least one intermediate wall through which the inner space is subdivided into at least two horizontal chambers. With the provision of at least two horizontal chambers, further uses of the culture vessel and complex culturing methods are enabled. The intermediate wall can comprise, for example, a material which permits molecular diffusion, particularly of biologically active molecules, for example, growth or differentiation factors, a porous material and/or a material with pre-determined breaking sites. Advantageously, the intermediate wall enables a substance which is initially exclusively present in one of the horizontal chambers to be transferred at the start and/or during the culturing by diffusion and/or by a release through the pores and/or the pre-determined breaking sites into the other horizontal chamber. In this way, additional degrees of freedom are achieved for the culturing of the biological cells. For example, a molecular differentiation factor can diffuse through the intermediate wall by which the differentiation of biological cells in hanging droplets is influenced.

The intermediate wall can extend over the entire inner space in order to form two separate horizontal chambers. In this case, the intermediate wall is provided, for example, as part of the bottom section in order to release the liquid in the bottom section only after the opening of pre-determined breaking sites or to add a biologically active substance, temporally delayed, to the liquid in the bottom section. Alternatively, the intermediate wall can be part of the cover section in order to form therein the culturing area on the side facing toward the bottom section. In this case, biologically active substances can diffuse from the horizontal chamber which is separated from the remaining inner space of the culture vessel by the intermediate wall into the hanging droplets.

According to a further advantageous embodiment of the invention, the culture vessel is provided with a carrier device which supports the culture vessel at its underside. When the culture vessel is in use, the carrier device is located at the side facing in the direction of gravity, in particular on the bottom section of the culture vessel. Advantageously, the carrier device enables stable positioning of the culture vessel on a platform, for example, a laboratory bench or in an automated culturing system. Preferably, the carrier device comprises support feet which are arranged distributed at the bottom section of the culture vessel.

If, according to a further variant of the invention, the carrier device has mass elements with which a mass center of gravity of the culture vessel is formed, particularly during use, in the bottom section or adjacent thereto, the carrier device can advantageously also perform a stabilizing function. Particularly on use of a vessel wall manufactured from a flexible film, the culture vessel is stabilized on the underside with the mass elements of the carrier device. An undesirable irregular deformation, for example, of a bag-shaped culture vessel and thus an undesirable movement of the cell suspension are avoided.

According to the invention, the culture vessel has a closed inner space which is delimited on all sides by the cover and bottom sections, possibly in combination with the side section. In order to simplify influencing the culturing of biological cells in the closed inner space, according to a further embodiment of the invention, the culture vessel is preferably provided with a media device having at least one closable media interface, particularly preferably at least two media interfaces, which is configured for the supply and removal of liquid and/or gaseous media into and out of the inner space. The at least one media interface comprises, for example, a tube connector, an opening with a cover, or a wall section which can be bored through by lines for the liquid and/or gaseous media.

Advantageously, according to a further modification of invention, the vessel wall of the culture vessel is provided with at least one window section which enables optical and/or mechanical access to at least one of the hanging droplets. According to a variant, the at least one window section can be configured for optical observation of the at least one hanging droplet. In this case, the at least one window section preferably comprises a planar, plate-shaped region which is made of an optically transparent material in the cover section. Alternatively or additionally, the at least one window section can be configured for invasive penetration by a tool. For this purpose, the window section can have, for example, a pre-determined breaking site in the cover section which is arranged adjacent to the position of a holding element on the culturing area.

If a deformable vessel wall is used, embodiments of the culture vessel are possible in which the outer form of the culture vessel is changeable by means of mechanical influences. In order to avoid undesirable deformations, according to a further advantageous embodiment of the invention, an outer receptacle device for the culture vessel is provided which is configured for receiving the vessel wall. The outer receptacle device, e.g. in the form of a box, possibly with perforations for feeding through media lines, forms a protection and a contact surface for the vessel wall. Preferably, the outer receptacle device has a transparent plate against which the cover section lies if, during use of the culture vessel, the working distance between the cover and bottom sections is adjusted and the culturing of the cells takes place in the hanging droplets. The transparent plate forms a planar delimitation of the cover section, for example, in the form of a resilient film, by which means an observation of the hanging droplets with a visual observation device is facilitated.

Alternatively or additionally, according to a further modification of the invention, the culture vessel can be provided with an outer clamping device. The clamping device is arranged in an edge region of the vessel wall in order to adjust the volume of the inner space of the culture vessel. On actuation of the outer clamping device, the volume of the inner space can be reduced, for example, by means of rolling up or squeezing part of the vessel wall, wherein the pressure in the inner space increases.

According to a further advantageous embodiment of the invention, the cover and bottom sections are provided with line-shaped coupling elements. On deformation of the culture vessel such that the cover and bottom sections touch one another, a connection of the cover and bottom sections can be provided along the line-shaped coupling elements. Advantageously, this enables the subdivision of the inner space of the culture vessel into vertical chambers in which, for example, different culturing conditions can be set.

The culture vessel according to the invention has particular advantages in relation to its simple use and the provision of a closed system. The separation of the inner space from the surroundings enables sterile culturing conditions, exact and reproducible control of the culturing conditions and the fulfillment of requirements of culturing protocols (such as good manufacturing practice—GMP). The change of media, the harvesting of the cultured cells and the addition of differentiation factors can take place at high speed and a plurality of hanging droplets can be formed simultaneously. The technique according to the invention is therefore suitable for uses with a high throughput ("high throughput method").

BRIEF DESCRIPTION OF THE DRAWINGS

Further details and advantages of the invention are described below making reference to the accompanying drawings, which show in.

DETAILED DESCRIPTION OF PREFERRED EMBODIMENTS

Preferred embodiments of the invention will now be described making reference to the design of the culture vessel and the carrying out of the method for culturing biological cells. Details of the culturing method are not given, provided these are known from conventional methods for culturing biological cells for multiplication and/or differentiation purposes, particularly in hanging droplets. Culturing conditions, particularly the selection of culturing media, the design of culturing protocols (the supply and removal of particular media according to a particular time plan) and physical conditions such as, for example, the temperature, pressure, air humidity and lighting can be provided, as known from conventional culturing methods. The use of the invention is not restricted to the culturing of particular types of cells, but is applicable to a variety of cell types and particularly differentiated cells, stem cells or cell groups. However, the culturing of human embryo stem cells is precluded from the scope of protection.

Embodiments of the invention are described making exemplary reference to culture vessels which are configured for manual use, for example, in a laboratory. The invention is not restricted to the exemplary forms and sizes described, but is also usable accordingly with culture vessels which are adapted to other uses such as, for example, in automated culturing systems.

Figure 1:
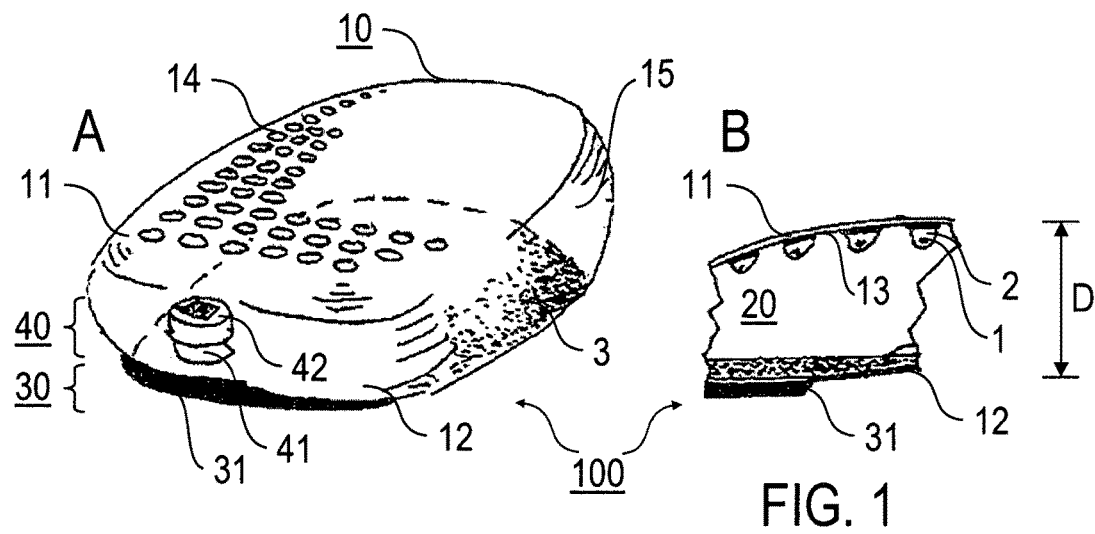
FIGS. 1A and 1B schematic illustrations of a first embodiment of a culture vessel according to the invention.

FIG. 1 shows a first embodiment of the culture vessel 100 according to the invention in a perspective view (FIG. 1A)

and as a portion thereof in a sectional view (FIG. 1B). The culture vessel 100 comprises a vessel wall 10 which is made of a flexible plastics material, in particular a biocompatible polymer film, for example, polyethylene or ethylene vinyl acetate. The vessel wall 10 forms a flexible bag with an areal, flattened form extending, on use of the culture vessel 100, in the horizontal direction. At a first side (upper side) of the vessel wall 10, the polymer film forms a cover section 11 and at a second side (lower side) a bottom section 12. The bottom section 12 has the form of a flat basin which is provided for receiving a liquid 3 (cell suspension). The curved wall section at which the cover and bottom sections 11, 12 are connected to one another is designated the side section 15. An inner space 20 is enclosed on all sides by the cover, bottom and side sections 11, 12, 15, the culturing of biological cells taking place in said inner space in hanging droplets. The cover and bottom sections 11, 12 are substantially areally extending wall sections, with a mutual spacing D, which are curved at their edges toward the side section 15.

The inner surface of the cover section 11 forms the culturing area 13 which is provided for the culturing of the biological cells in hanging droplets. Holding elements 14 are arranged on the culturing area 13. The holding elements 14 are configured for the positioning of the droplets 2 (see FIG. 1B) and are arranged distributed over the whole culturing area 13 (partially shown in FIG. 1A). The arrangement of the holding elements 14 comprises, for example, a regular matrix arrangement with straight rows and columns.

In the embodiment of the culture vessel 100 shown, the holding elements 14 comprise hydrophilic surface regions of the culturing area 13 which are separated from one another by means of the otherwise hydrophobic surface of the culturing area 13. The local hydrophilic surface regions are surrounded on all sides along the culturing area 13 by the hydrophobic surface. Alternatively or additionally, the holding elements 14 can comprise step-shaped microstructures which have a liquid attracting effect (see FIGS. 16 to 20).

The culture vessel 100 is provided with a carrier device 30 which is arranged on the outside of the vessel wall 10, particularly on the outside of the bottom section 12. The carrier device 30 comprises an annular mass element 31 which is manufactured, for example, from a plastics material, optionally with a metal insert. With the mass element 31, the culture vessel 100 rests on a support, for example, a laboratory bench or in a holder (not shown). The mass element 31 is formed such that the center of mass of the culture vessel 100 lies in the bottom section 12 or adjacent thereto. This enables the culture vessel 100, although it is made of a deformable flexible bag, following a movement, to be brought easily into a position in which the cover section 11 is located on the side of the culture vessel 100 facing upwardly (opposite the direction of gravity).

The culture vessel 100 is further provided with a media device 40 which, in the embodiment shown, comprises a filling opening 41 with a cover 42. The cover 42 can have a marking, for example, an optical code (bar code, QR code) for example for identification purposes. The filling opening 41 comprises an attachment pipe element made, for example, of plastics material which is firmly attached to the side section 15 and carries the cover 42.

The culture vessel 100 has two operating states. In a first operating state (unfolded state), the vessel wall 10 is spanned so that a working distance D is formed between the cover section 11 and the bottom section 12 which is at least twice as large as the diameter of the hanging droplets 2, in particular larger than 5 mm, for example, 100 mm. In the unfolded state of the culture vessel 100, the droplets 2 with the biological cells 1 can hang freely on the downwardly facing culturing area 13 of the cover section 11 without touching other parts in the inner space 20, particularly the liquid 3 in the bottom section 12. In a second operating state (compressed state), the vessel wall 10 is deformed so that the culturing area 13 touches the liquid 3 in the bottom section 12. In the compressed state, the culturing area 13 is wetted by the liquid 3. It is possible to switch between the two operating states by exerting a force acting on the vessel wall 10, particularly in the inner space 20 or in the side section 15. In the compressed state, the loading of the culturing area 13 with the liquid 3 takes place whilst, in the unfolded state, the culturing of the cells 1 in the hanging droplets takes place.

The culturing according to the invention of the biological cells 1 in the hanging droplets 2, particularly with the culture vessel 100 of FIG. 1 comprises the following steps. The culture vessel 100 rests on a carrier platform (not shown). Firstly the liquid 3, comprising a cell suspension of, for example, human pluripotent stem cells in a culture medium, is provided on the bottom section 12 of the culture vessel 100. The cell suspension is fed through the filling opening 41 into the bottom section 12 so that said bottom section is covered with a liquid layer with a thickness of, for example, 10 mm. Subsequently, a gaseous medium, for example an air-$CO_2$ mixture with 5% $CO_2$ is admitted to the inner space 20 through the filling opening 41 so that the unfolded state of the culture vessel 100 is formed. Due to a residual stiffness of the polymer film of the vessel wall 10, the unfolded state is preserved until the closure of the filling opening 41 with the cover 42.

Following the pressure-tight closure of the filling opening 41 with the cover 42, compression of the culture vessel 100 takes place such that the distance between the cover section and the bottom section 12 is reduced. For this purpose, for example, pressure is applied manually or with a tool on the upper side of the culture vessel 100. The flexibility of the material of the vessel wall 10 and the compressibility of the gas present in the inner space 20 permit the immersion of the culturing area 13 into the liquid 3. Following the wetting of the culturing area 13, a restoration of the vessel wall 10 takes place wherein, under the effect of the internal pressure in the inner space 20, the working distance D between the cover section 11 and the bottom section 12 is created. The liquid 3 adhering to the culturing area 13 is collected on the holding elements 14 where the hanging droplets 2 form. Subsequently, the culturing of the cells 1 in the hanging droplets 2 takes place, according to the desired culturing protocol. In the closed inner space 20, an atmosphere saturated with water vapor exists over the liquid 3 so that the cells 1 in the hanging droplets 2 can be cultured over days or weeks without the hanging droplets becoming smaller due to evaporation.

In a practical example, the culture vessel 100 has the following dimensions: cover section 11 and bottom section 12: 20 cm·20 cm, working distance D: 3 cm, liquid volume in bottom section 12: 80 ml, diameter of hanging droplets 2: 3 mm, number of hanging droplets 2: 150.

The formation of the unfolded state of the culture vessel 100 by means of a raised internal pressure in the inner space 20 is not necessarily required. Alternatively, the unfolded state can be set using an elastic restoring force which is created by the material of the vessel wall 10, particularly in the side section 15. This embodiment of the invention is shown schematically in FIG. 2. FIGS. 2A and 2C illustrate the unfolded state, whereas FIG. 2B illustrates the compressed state of the culture vessel 100 in a perspective, sectional view.

Figure 2:
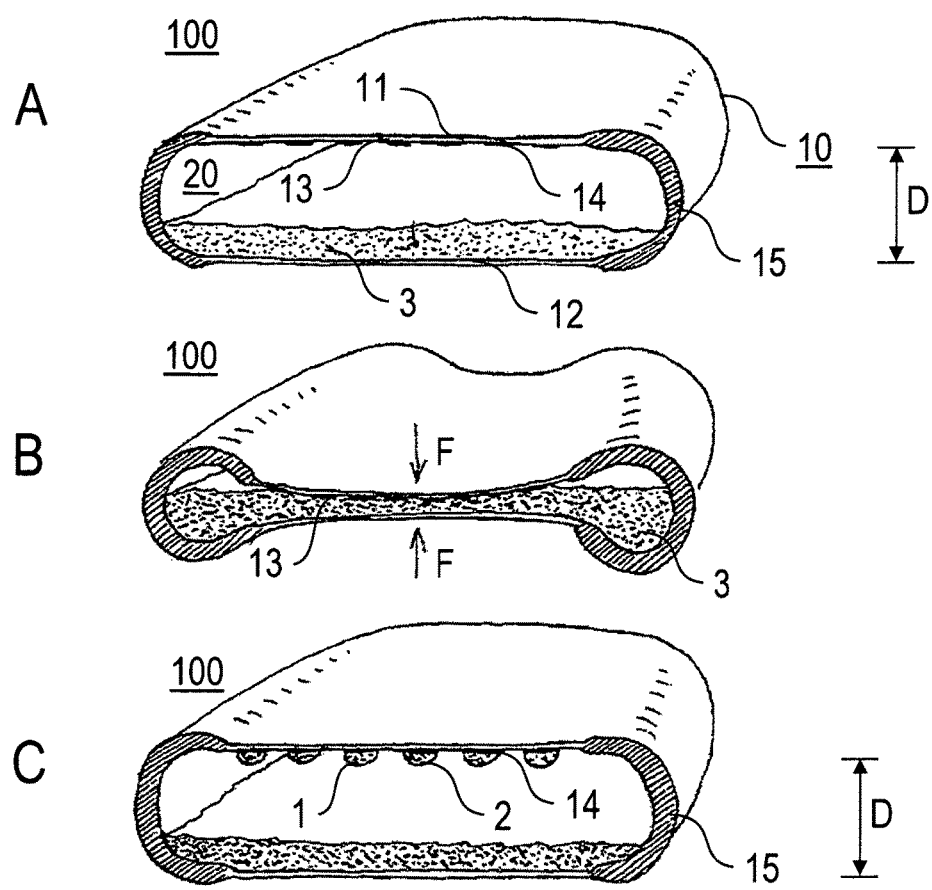
FIGS. 2A to 2C a schematic illustration of the formation of hanging droplets according to a preferred embodiment of the culturing method according to the invention.

The culture vessel 100 according to FIG. 2 comprises, as described above, a cover section 11 for providing the culturing area 13 for receiving the hanging droplets 2, a bottom section 12 for receiving the liquid 3 and a side section 15. The portions 11, 12 and 15 enclose the inner space 20. The cover and bottom sections 11, 12 in the unfolded state are planar layers of a flexible material, for example, deformable plastics films. The planar form of the cover and bottom sections 11, 12 is formed by their own form-holding ability and is formed in that they are stretched by means of the side section 15. The side section 15 is made of an elastic material, for example, silicone which has an internal pre-tension and exerts an elastic restoring force on the vessel wall 10. The culture vessel 100 is provided with a media device which can comprise a filling opening according to FIG. 1 or another media interface (see below), not shown in FIG. 2. Furthermore, the culture vessel 100 of FIG. 2 can be provided with a carrier device (not shown) for supporting the culture vessel 100.

FIG. 2A shows the culture vessel 100 at the start of the culturing method. The liquid 3, particularly a cell suspension, is arranged in the bottom section 12. The culturing area 13 has the working distance D from the bottom section 12 due to the spanning effect of the side section 15. The liquid 3 is located, due to its gravitational force, on the inside of the bottom section 12.

FIG. 2B shows the compressed state of the culture vessel 100. Under the effect of an external force F which acts on at least one of the cover and bottom sections 11, 12, the culturing area 13 on the inside of the cover section 11 is immersed in the liquid 3. Die culturing area 13 is wetted so that the liquid 3 can be collected on the holding elements 14 (hydrophilic surface regions of the culturing area 13).

On provision of the compressed state, the force F acting from outside is exerted, for example, manually or with an external actuating device (not shown). The use of an external actuating device has the advantage that it enables a controlled stepless movement during compression and during restoration. The stepless movement has an advantageous effect on the avoidance of the falling of droplets during the restoration movement.

Once the effect of the external force F is removed, the restoration of the culture vessel 100 into the unfolded state takes place (FIG. 2C). The restoration is brought about by the elastic restoring force of the side section 15. The hanging droplets 2 with the biological cells 1 have collected on the holding elements 14. In the unfolded state, the further culturing of the cells 1 takes place in the hanging droplets 2, according to the desired culturing protocol.

A particular advantage of the embodiment according to FIG. 2 lies therein that the form and tension, particularly of the cover section 11, is provided by the elastically resilient side section 15. By this means, the cover section 11 comprising, for example, a transparent polymer film is pulled flat and is oriented horizontally. This is advantageous for observation of the hanging droplets, for example, using a microscope, since when using an optically clear film and an objective lens with a large aperture, the cells 1 can be imaged and observed directly in the hanging droplets. The optionally also provided tightness and horizontal orientation of the bottom section 12 has the advantage that illumination of the culture vessel from the underside is enabled. Furthermore, the liquid 3, particularly cells in the cell suspension in the bottom section 12 can be observed, for example, with a microscope.

Figure 3:
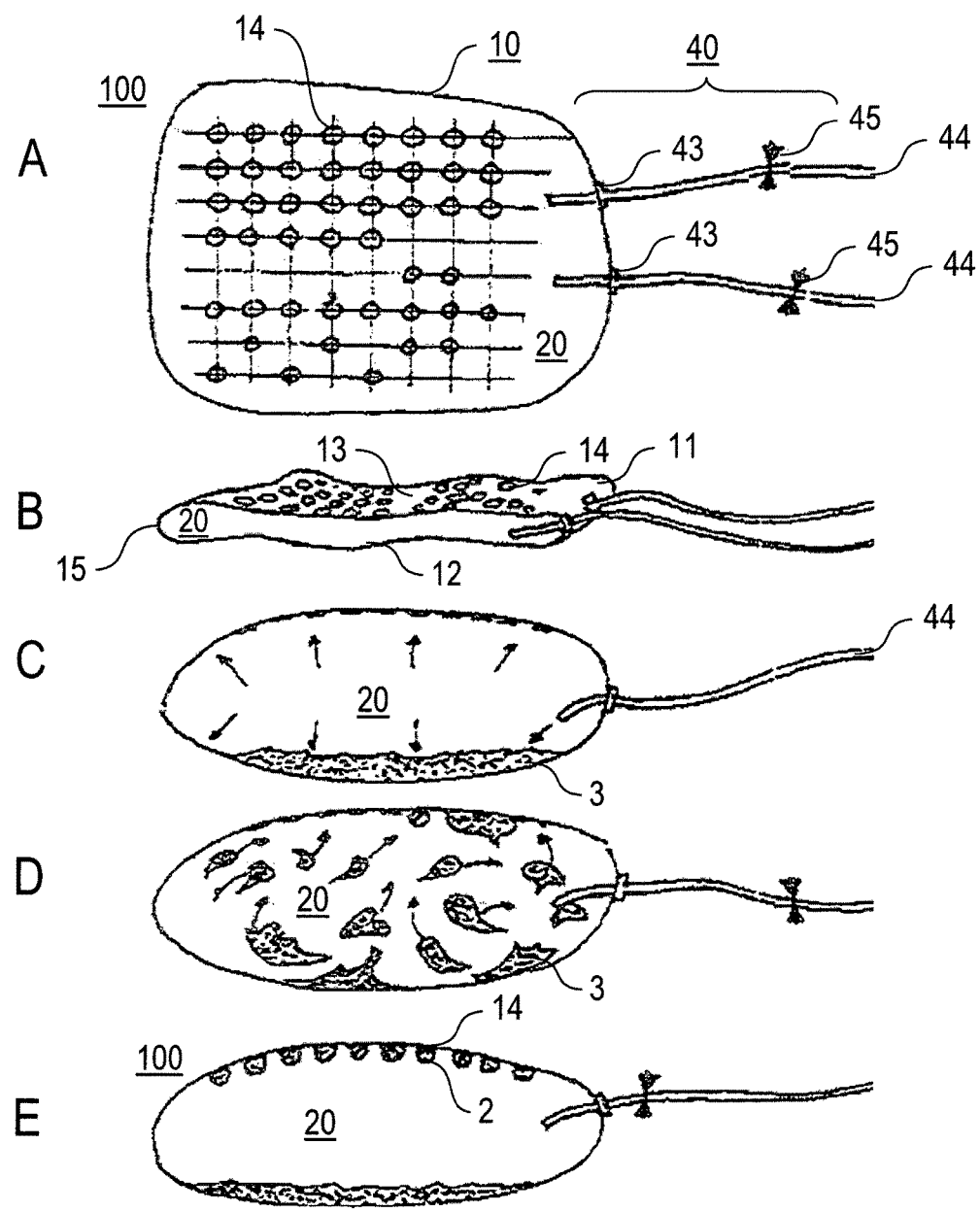
FIGS. 3A to 3E further illustrations of variants of the culturing method according to the invention.

FIG. 3 illustrates a further embodiment of a bag-shaped culture vessel 100 in different operating states. The culture vessel 100 comprises a vessel wall 10 made of a plastics film with the areal cover and bottom sections 11, 12 which are connected to one another at their edge regions. The curved transition region between the cover and bottom sections 11, 12 is also designated as side section 15. The media device 40 comprises two media interfaces 43 (line passages through the vessel wall 10). The media interfaces 43 are configured for a gastight and airtight coupling of the tubes 44 to the side section 15. Each of the media interfaces 43 enables the passage of a tube 44, each with a control valve 45 into the inner space 20 of the culture vessel 100. The tubes lead to external reservoirs (not shown) for gaseous or liquid media. Deviating from the illustration, a single tube 44 or more than two tubes 44 can be provided.

FIGS. 3A and 3B show the bag-shaped culture vessel 100 in the unfilled, sterile starting state in a plan view and in a sectional perspective view. The inner space 20 is empty. The inner side of the cover section 11 forms the culturing area 13 with the holding elements 14 which are arranged with a pattern of rows and columns.

At the start of the culturing of biological cells according to the invention, the culture vessel 100 is filled according to FIG. 3C. The liquid 3 is fed via a first tube 44 to the bottom section 12, whilst via a second tube (not shown), a gaseous medium, for example an air-$CO_2$ mixture with 5% $CO_2$ is fed in. Under the effect of the gaseous medium, an internal pressure builds up in the inner space 20 so that the culture vessel 100 reaches the unfolded state.

The method illustrated in FIG. 3 shows that the hanging droplets in the culture vessel 100 must not necessarily be realized by means of a deformation of the vessel wall, but by means of its movement as a whole. In order to load the culturing area 13, the culture vessel 100 is pivoted as per FIG. 3D. For this, the tubes 44 are preferably closed. The liquid 3 is distributed in the inner space 20 so that the hanging droplets 2 form on the holding elements 14 (FIG. 3E). In the unfolded state according to FIG. 3E, when needed, tubes are opened again in order to feed in supplementary gaseous medium in order to maintain the form of the culture vessel 100 during culturing.

The culture vessel 100 according to FIG. 3 has the special advantage that it is particularly suitable for the combination of the culturing with cryopreservation of the cultured cells. The vessel wall can be manufactured from low temperature-stable materials so that the culture vessel 100 can be directly frozen with the hanging droplets during or after the culturing without further intermediate steps and can be subjected to conservation cooling (storage at low temperatures).

Figure 4:
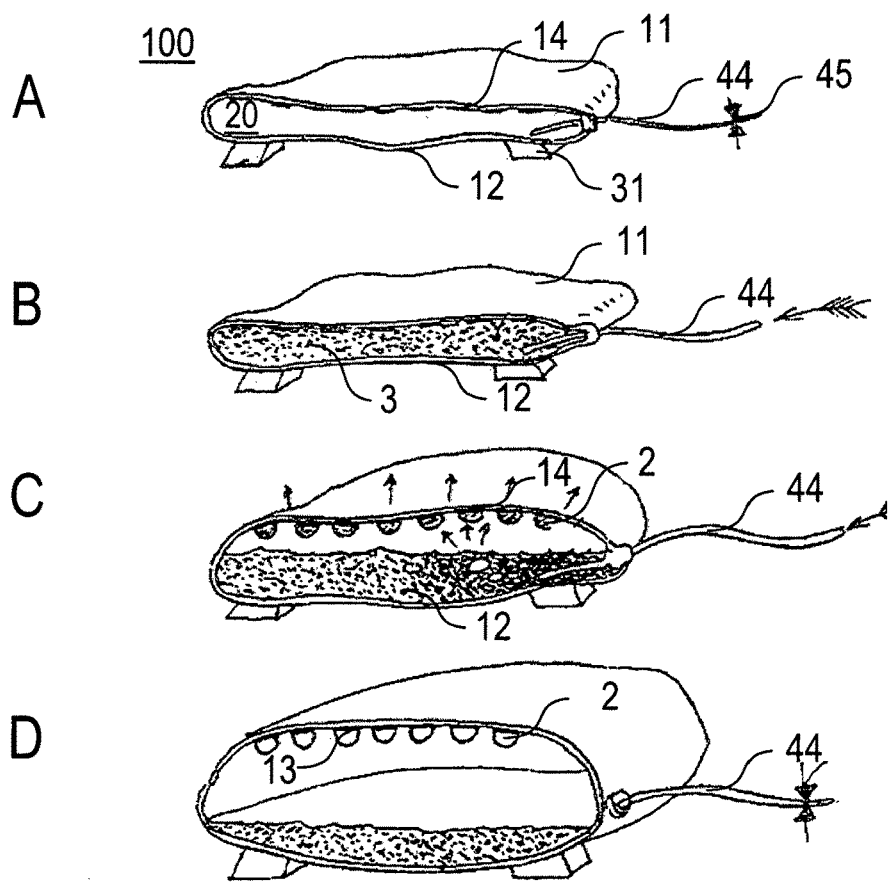
FIGS. 4A to 4D a schematic illustration of a further embodiment of the culture vessel according to the invention which is provided with a carrier device.

FIG. 4 shows a further variant of the method according to the invention wherein hanging droplets 2 are formed on the culturing area 13 of the culture vessel 100 according to the invention. According to FIG. 4A, the culture vessel 100 is configured, as shown in FIG. 3B, in the form of a flexible bag, wherein additionally a carrier device 30 with mass elements 31 is provided on the bottom section 12. Before the loading with the liquid, the culture vessel 100 has a sterile, interfolded inner space 20. The tube 44 is closed with the control valve 45. The mass elements 31 act as stabilizing support feet on the underside of the culture vessel 100.

The state of the culture vessel 100 in FIG. 4A corresponds to the compressed state in which the cover and bottom sections 11, 12 are brought close to one another. Accordingly, the charging of the culture vessel 100 with the liquid 3 and the loading of the culturing area on the inside of the cover section 11 according to FIG. 4B can take place in a common method step. Only the liquid 3 is fed in without unfolding the culture vessel 100 with a gaseous medium.

After the wetting of the culturing area according to FIG. 4B, in a further step, the transition to the unfolded state of the culture vessel 100 takes place (FIG. 4C). For this purpose, a gaseous medium is forced into the culture vessel 100 via a tube 44, so that the bag bulges, the holding elements 14 are separated from the liquid 3 on the bottom 12 and the hanging droplets 2 are formed.

In the tightly filled state (FIG. 4D), the desired working distance of the culture vessel 100 is achieved. In this state, the tube 44 is closed gastight. Subsequently, the culturing of the hanging droplets 2 with the biological cells follows, according to the desired culturing protocol.

Figure 5:
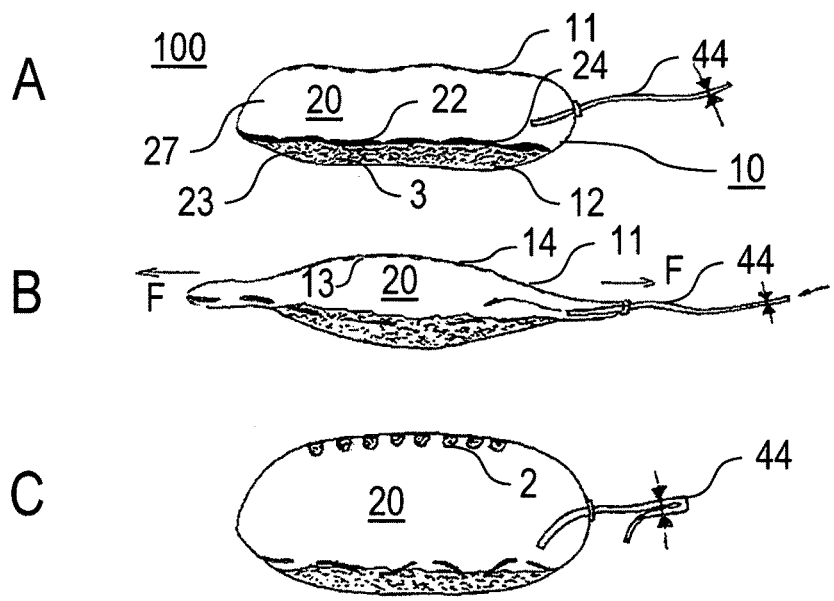
FIGS. 5A to 5C a schematic illustration of further variants of the method according to the invention.

FIG. 5 shows a further embodiment of the culture vessel 100 according to the invention, the vessel wall 10 of which, together with the cover and bottom sections 11, 12 encloses the inner space 20. The inner space 20 is divided by an intermediate wall 22 into two horizontal chambers 23, 27. The lower horizontal chamber 23 is provided for receiving the liquid 3 on the bottom section 12. The upper horizontal chamber 27 is provided for receiving a gaseous medium for forming the unfolded state of the culture vessel 100. The intermediate wall 22 contains pre-determined breaking sites 24 at which openings can be formed in the intermediate wall 22 on application of a mechanical force.

FIG. 5A shows the culture vessel 100 in a starting state. The lower horizontal chamber 23 is pre-filled with the liquid 3, for example, a sterile solution such as a culture medium for biological cells. The liquid 3 is separated from the remaining inner space 20 by the intermediate wall 22. The upper horizontal chamber 27 can be filled via the tube 44 with a gaseous medium so that the upper horizontal chamber 27 is partially or completely unfolded. Typically, the filling of the upper horizontal chamber 27 with the gaseous medium takes place immediately before the use of the culture vessel 100 only.

For the culturing of biological cells in hanging droplets, the culture vessel 100 is pulled across its width by externally acting forces F so that the cover and bottom sections 11, 12 approach one another and simultaneously the pre-determined breaking sites 24 of the intermediate wall 22 tear open (FIG. 5B). A cell suspension with the cells to be cultured is flushed into the inner space 20 via the tube 44 so that the cell suspension mixes with the liquid 3. The culturing area 13 on the inside of the cover section 11 is wetted with the mixture of the liquid 3 and the cell suspension so that the hanging droplets 2 form on the holding elements 14 (hydrophilic regions). Subsequently, by feeding in gaseous medium, the culture vessel 100 is brought into the unfolded state (FIG. 5C) in which the further culturing takes place according to the desired culturing protocol. After formation of the unfolded state, tubes are closed (e.g. clamped) and separated from external reservoirs.

Figure 6:
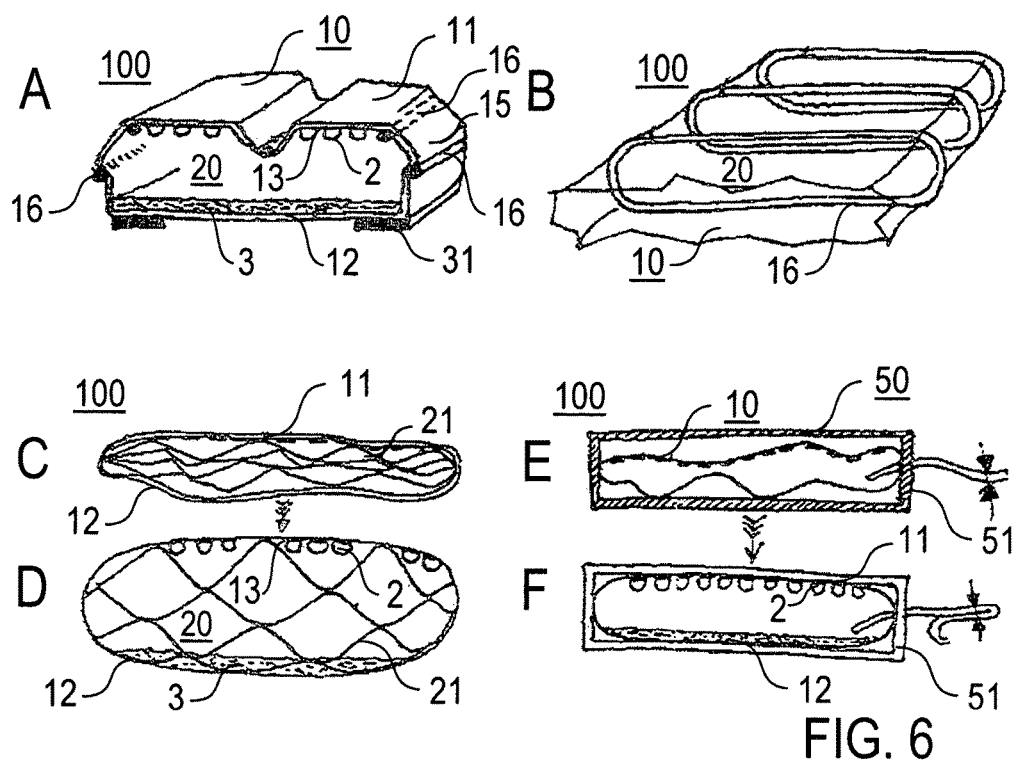
FIGS. 6A to 6F schematic illustrations of further embodiments of the culture vessel according to the invention.

FIG. 6 shows further variants of the culture vessel 100 according to the invention partly in a perspective sectional partial view (FIG. 6A), in a phantom view (FIG. 6B) or in sectional views (FIGS. 6C-6F).

According to FIG. 6A, the vessel wall 10 with the cover, bottom and side sections 11, 12, 15 also comprises stiffening elements 16, for example, in the form of rods which extend in the horizontal and/or vertical direction. The bottom section 12 comprises, for example, a rigid bottom trough for receiving the liquid 3. Arranged on the underside of the bottom trough are mass elements 31. In the region of the cover and side sections 11, 15, the vessel wall 10 comprises a plastics film material which is spanned with stiffening elements 16. The stiffening elements 16 consist of an elastically deformable plastics material, for example, silicone which generates elastic restoring forces when deformed. The form of the inner space 20 can be determined by the form and arrangement of the stiffening elements 16, depending on the actual use conditions. In order to form the compressed state of the culture vessel 100, the cover section 11 is brought close to the bottom section 12 against the elastic restoring forces by the stiffening elements 16 until the culturing area 13 on the inside of the cover section 11 is wetted with the liquid 3 and the hanging droplets 2 are formed.

According to FIG. 6B, the stiffening elements 16 are formed in the form of rings of an elastic material. The rings are fastened, for example welded, onto the inside of the vessel wall 10. The form of the culture vessel 100 in the unfolded state is determined by the form and arrangement of the stiffening elements 16. For compression of the culture vessel 100, an external force is applied for deformation of the vessel wall 10 and in particular the stiffening elements 16.

In FIGS. 6C and 6D, an embodiment of the culture vessel 100 according to the invention is shown, wherein a foldable inner carrier 21 is provided in the inner space 20. The foldable inner carrier 21 consists, for example, of an elastically deformable wire mesh of a biocompatible material or an elastically deformable plastics mesh. In the compressed state of the culture vessel 100 (FIG. 6C) the inner carrier 21 is pressed together so that, as described above, the culturing area on the inside of the cover section 11 can be wetted with the liquid (not shown) on the bottom section 12. Following the unfolding of the inner carrier 21 (FIG. 6D) the desired working distance is set between the cover and bottom sections 11, 12. Parts of the liquid have collected on the culturing area 13 in the form of hanging droplets 2.

According to FIGS. 6E and 6F, the culture vessel 100 according to the invention, e.g. as per FIG. 3, is provided with an external receptacle device 50. The receptacle device 50 has the form of a cuboid box with planar box walls 51. The box is configured for receiving the vessel wall 10 in the compressed (FIG. 6E) and in the unfolded state (FIG. 6F). In the unfolded state, the box walls form support surfaces for the vessel wall 10 so that particularly the cover section 11 with the hanging droplets 2 is given a planar horizontal orientation in the unfolded state. The internal dimension of the box is selected such that when an internal pressure is applied to the culture vessel and the cover and bottom sections 11, 12 are placed on the upper and lower box walls 51, the desired working distance is formed for receiving the hanging droplets 2.

Advantageously, at least one of the upper and lower box walls 51 can be made of an optically clear, transparent material. In this case, observation of the hanging droplets 2, particularly with a microscope is also possible during culturing whilst the culture vessel 100 is arranged in the receptacle device.

Figure 7:
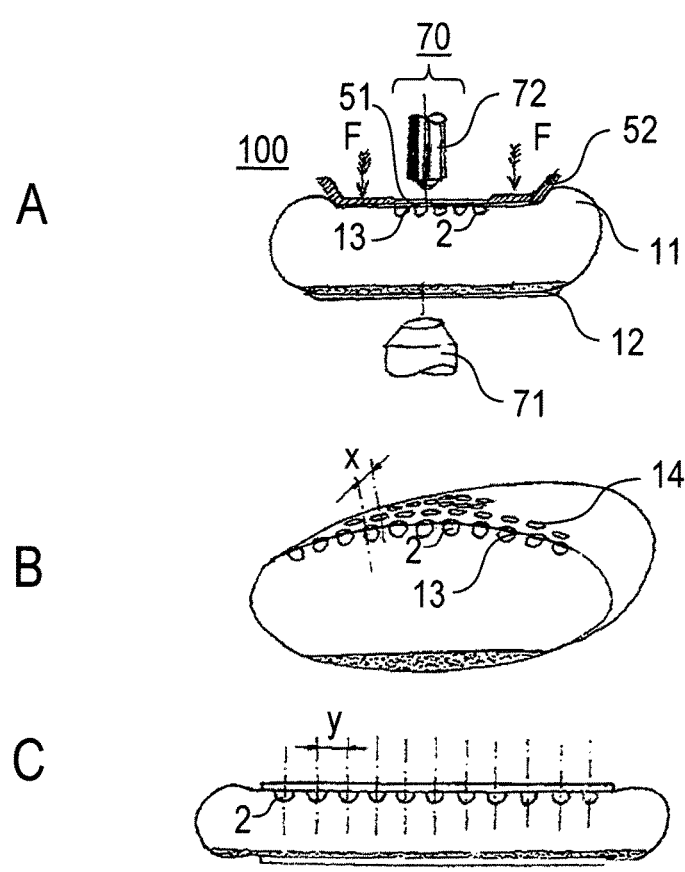
FIGS. 7A to 7C a schematic illustration of the optical observation of hanging droplets in the culture vessel according to the invention.

FIG. 7 shows further details of the invention which are significant for the microscopic observation of the culturing and/or automation of the culturing. In FIG. 7A, the culture vessel 100 e.g. as per FIG. 3, is shown in an unfolded state. The hanging droplets 2 are situated on the culturing area 13 on the inside of the cover section 11 with the desired working distance from the bottom section 12. An observing device 70 such as, for example, a microscope (not shown fully) comprises an illumination device 71 beneath the bottom section 12 and an objective lens 72 above the cover section 11. Provided on the outside of the cover section 11 is a planar plate 52 with an optically clear, transparent window 51. The plate 52 has chamfered edge sections on its outer edges. The edge sections advantageously stabilize the position of the plate 52 on the cover section 11. When external forces F are applied, the plate 52 is partially pressed into the culture vessel 100 so that a lateral displacement is prevented. The planarity of the vessel wall in the cover section 11 is improved with the plate 52. The hanging droplets 2 can be optically detected through the window 51 with the observing device 70. Alternatively, the plate 52 can be, for example, part of a receptacle device 50 in FIG. 6E.

If the holding elements 14 of the culturing area 13 have pre-determined, known positions and form a particular geometrical, preferably regular pattern, there are advantages for automation of the observation with the observing device 70. If the holding elements 14 are arranged, for example, in straight rows and columns with row spacings x and column spacings y (see FIGS. 7B and 7C), the individual hanging droplets 2 can be approached by the objective lens 72 (see FIG. 7A) in a facilitated manner. Using the observing device 70, for example, the temporal progress of growth and/or differentiation processes can be documented. FIG. 7B shows that the microscopic observation of the hanging droplets 2 is also possible without the plate 52. Focusing for the microscopic imaging is improved, however, if the plate (see FIGS. 7A, 7C) is used.

According to a further variant of the invention, an arrangement of optical elements, for example, a lens arrangement, can be provided on the outside of the vessel wall of the culture vessel according to the invention or on a plate placed on the vessel wall in order to facilitate the optical observation of the hanging droplets. The provision, for example, of lens arrangements comprising a plurality of lenses which are each focused on one of the hanging droplets enables the integration of lens-free microscope arrays and facilitates a permanent monitoring of the culturing in the hanging droplets.

Figure 8:
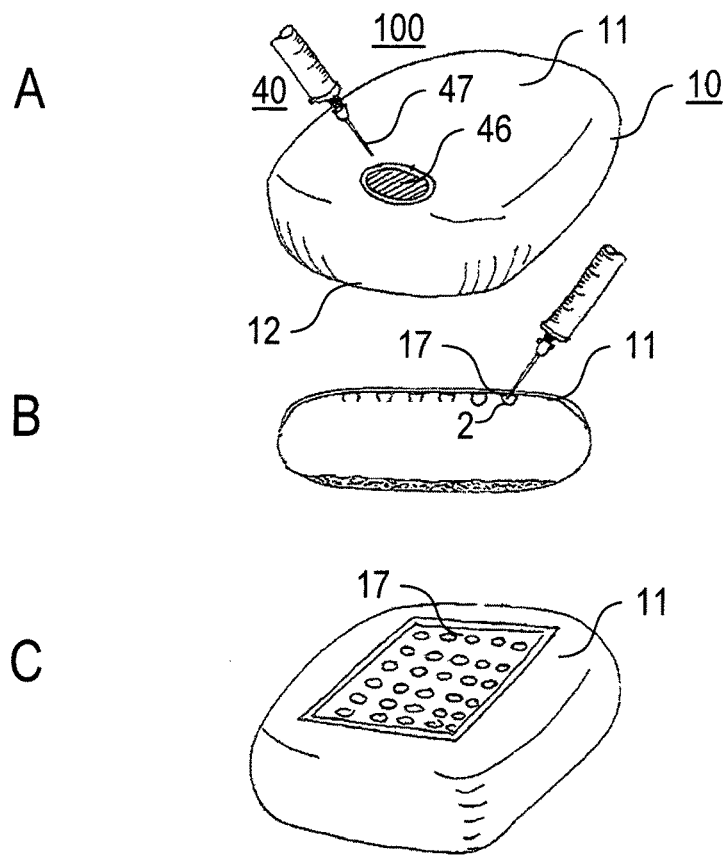
FIGS. 8A to 8C a schematic illustration of accessing of hanging droplets with an external tool.

An important feature of the culture vessel according to the invention lies therein that the inner space 20 (see e.g. FIG. 1) is closed relative to the surroundings. In order nevertheless to enable access to the inner space 20, the culture vessel 100 is preferably provided with the media device 40 which according to the embodiments in FIGS. 1 and 3 is configured for reversible opening and closing of the culture vessel 100. FIG. 8 shows further variants of a media device 40 which is configured for reversible or irreversible opening of the culture vessel 100.

According to FIG. 8A, the vessel wall 10 contains, particularly in the cover section 11, a septum 46 via which liquid or gaseous media can be introduced or removed by means of a cannula 47. For example, the septum 46 can be penetrated with the injection cannula of a syringe in order to feed liquid to the bottom section 12. Alternatively, access to the hanging droplets 2 through corresponding window sections 17 in the cover section 11, as shown in FIGS. 8B and 8C is possible. In particular, according to FIG. 8C, a window section 17 with pre-determined breaking sites can be integrated into the cover section 11, the positions of said breaking sites being selected matching the positions of the holding elements on the culturing area on the inside of the cover section 11. The breaking sites can be penetrated with a tool, for example a cannula, in order to feed additional substances to the hanging droplets and/or to remove samples from the hanging droplets.

Figure 9:
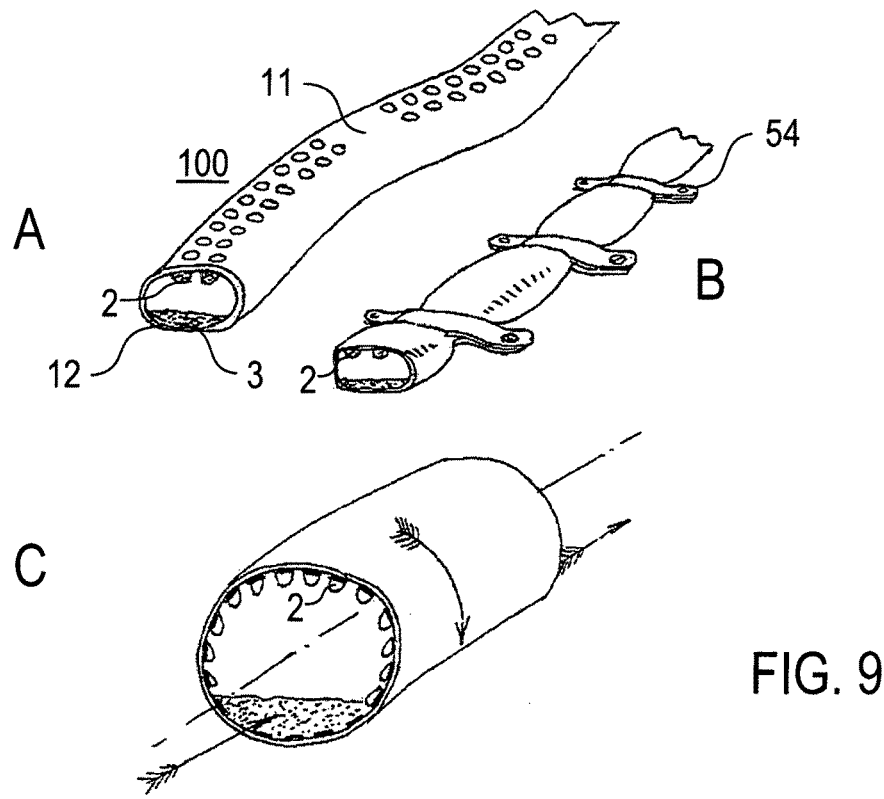
FIGS. 9A to 9C a schematic illustration of a further embodiment of a culture vessel according to the invention in the form of a tube.

The form of the culture vessel 100 according to the invention is not restricted to the flattened cushion or cuboid shape as described above making reference to FIG. 1 or 3. Alternatively, the culture vessel can have a tube form, as shown schematically in the perspective, sectional partial views of FIG. 9. According to FIG. 9A, the culture vessel 100 comprises a flattened deformable tube which is closable at its ends, made, for example, of plastics which extends in a longitudinal direction and has on a first longitudinal side (upper side) the cover section 11 for receiving the hanging droplets 2, and on a second longitudinal side (lower side), the bottom section 12 for receiving the liquid 3. According to FIG. 9B, the tube can be divided along the longitudinal direction with clamps 54. The clamps 54 fulfil a double function, firstly, of stabilizing the position of the tube on a support, for example, a laboratory bench and, secondly, of forming separate regions for the hanging droplets 2.

The charging of the culturing area 13 on the inside of the cover section 11 takes place by means of a deformation of the tube, as described above, for example, making reference to FIG. 1 or 2. Alternatively, as shown in FIG. 9C, a movement of the vessel wall 10 for wetting holding elements 14 with the liquid 3 can be provided. By means of a rotation about the longitudinal axis of the tube (see curved arrow), the liquid 3 flows via the holding elements 14 where, on further rotation, droplets remain hanging.

Figure 10:
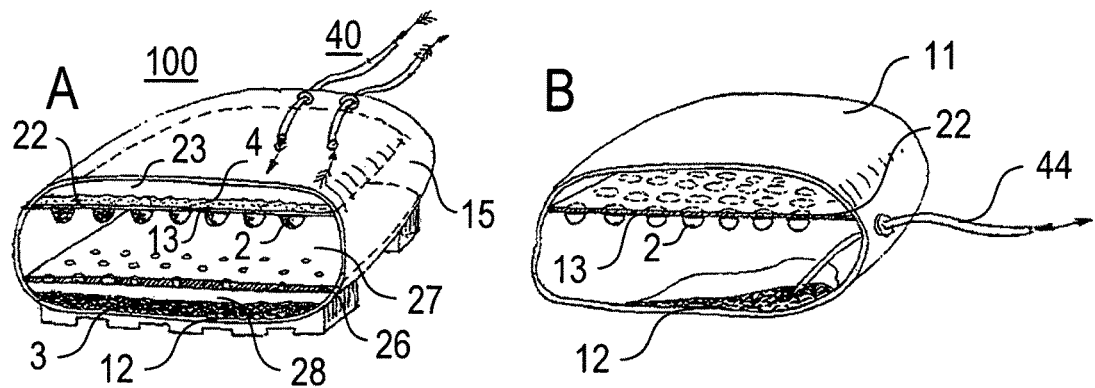
FIGS. 10A and 10B schematic illustrations of further embodiments of the culture vessel according to the invention with horizontal chambers.

In FIG. 10, further details of culture vessels 100 according to the invention are shown wherein additional degrees of freedom exist for influencing the hanging droplets. According to FIG. 10A, the inner space of the culture vessel 100 is divided by two intermediate walls 22, 26 into three horizontal chambers 23, 27, 28. The upper horizontal chamber 23 is filled by means of a media device 40 with a liquid 4. The middle horizontal chamber 27 is filled with a gaseous medium and temporarily contains liquid from the lower horizontal chamber 28. The lower horizontal chamber 28 contains a liquid 3. The shape of the culture vessel 100 in the unfolded state is determined, for example, by an elasticity of the side section 15.

The culturing area 13 is provided at the underside of the upper intermediate wall 22. The upper intermediate wall 22 enables molecular diffusion of substances from the liquid 4 into the hanging droplets 2. The diffusing substances comprise, for example, ions, differentiation factors, hormones or the like. The lower intermediate wall 26 comprises a perforated film which separates the liquid 3 in the lower horizontal chamber 28 from the horizontal chamber 27. The lower intermediate wall 26 offers protection to the hanging droplets 2 against unwanted liquid movements in the bottom section 12. If, due to a movement of the culture vessel 100, splashes of liquid fly upwardly, then these are collected by the lower intermediate wall 22.

The culturing method according to the invention takes place on use of the embodiment of FIG. 10A such that initially the liquid 3 is provided on the bottom section 12. Furthermore, the upper horizontal chamber 23 is filled with the liquid 4. The wetting of the culturing area 13 on the underside of the upper intermediate wall 22 is carried out, as described above, by means of a deformation of the culture vessel 100. By means of an external force, the cover and bottom sections 11, 12 are pressed toward one another. The liquid 3 penetrates through the lower intermediate wall 26 into the middle horizontal chamber 27 where the culturing area 13 is wetted. The liquid 3 collects on the holding elements of the culturing area 13 so that the hanging droplets 2 are formed following subsequent unfolding of the culture vessel 100. The addition of substances from the liquid 4 into the hanging droplets 2 takes place by diffusion during the culturing. For example, the differentiation of the cells in the hanging droplets 2 is influenced by means of differentiation factors.

Alternatively, the culture vessel 100 can have a single intermediate wall 22 adjoining the cover section 11. The culturing area 13 for receiving the hanging droplets 2 is formed on the underside of the intermediate wall 22. FIG. 10B shows the state of the hanging droplets 2 on the intermediate wall 22 at the end of a culturing process. If the cultured cells are to be collected, residual liquid is initially removed from the bottom section 12 via the tube 44. If needed, buffer or salt solutions for flushing processes can be fed in and out via the tube 44. Subsequently, the hanging droplets 2 with the cells or cell aggregates situated therein are shaken off the intermediate wall 22 so that they fall into the bottom section 12. There they are flushed off with a buffer solution which is fed in and out via the tube 44. The collected cells or cell aggregates can also be removed from the culture vessel 100 via the tube 44.

Figure 11:
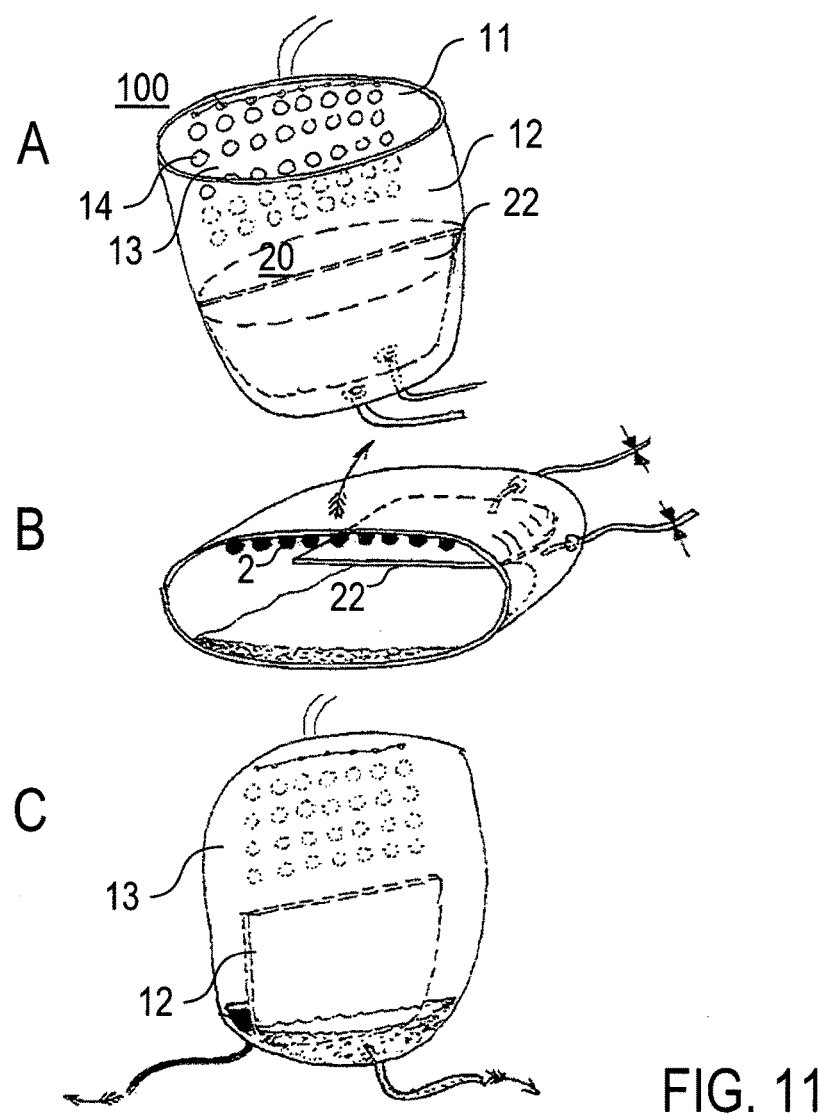
FIGS. 11A to 11C a schematic illustration of a further variant of the method according to the invention.

If an intermediate wall 22 extends only partially in the inner space 20 of the culture vessel 100 according to the invention, the collection (harvesting) of the cultured cells from the hanging droplets can be modified, as shown schematically in FIG. 11. FIG. 11A shows in a schematic, sectional perspective view, a bag-shaped culture vessel 100 with the cover section 11 and the bottom section 12 in a vertical orientation. The intermediate wall 22 extends over part, for example, half of the inner space 20. Holding elements 14 are provided on the culturing area 13 only in the region in which the intermediate wall 22 does not extend.

The charging of the culturing area 13 and the culturing of cells in hanging droplets takes place, as described above, for example, making reference to FIG. 1 or 2. Following ending of the culturing (FIG. 11B), the culture vessel 100 is rotated (see arrow). In order to collect (harvest) the cells or cell aggregates, these can be flushed in a targeted manner from the culturing area 13 into a subchamber on one side of the intermediate wall 22, whilst the originally present cell suspension remains on the opposite side of the intermediate wall 22 (see FIG. 11C).

Figure 12:
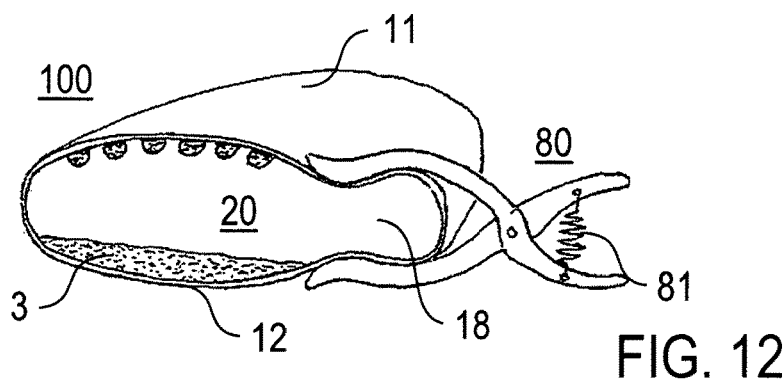
FIG. 12 a schematic illustration of the effect of an external clamping device.

FIG. 12 shows schematically a clamping device 80 with which the volume of the inner space 20 of a culture vessel 100 according to the invention can be influenced. If an internal pressure is applied to the culture vessel 100 to form the unfolded state, for example, according to FIG. 3C, gas losses can take place during the culturing lasting days or weeks. As a result, the culture vessel 100 could collapse in an undesirable manner. In order to prevent this, using the clamping device 80 which contains, for example, a spring drive 81, a constant pressure is exerted on the culture vessel 100 in a squeezing portion 18 of the vessel wall 10. By this means, the taut form of the bag and the adequate spacing of the hanging droplets 2 from the liquid 3 on the bottom section 12 is guaranteed even if gas losses occur. As an alternative to the variant in FIG. 12, the constant pressure can be maintained by means of a rolling-up portion at one side of the culture vessel, a separate bag portion to which a clamping device is applied or by means of an additional bag (not shown) attached via a tube.

Figure 13:
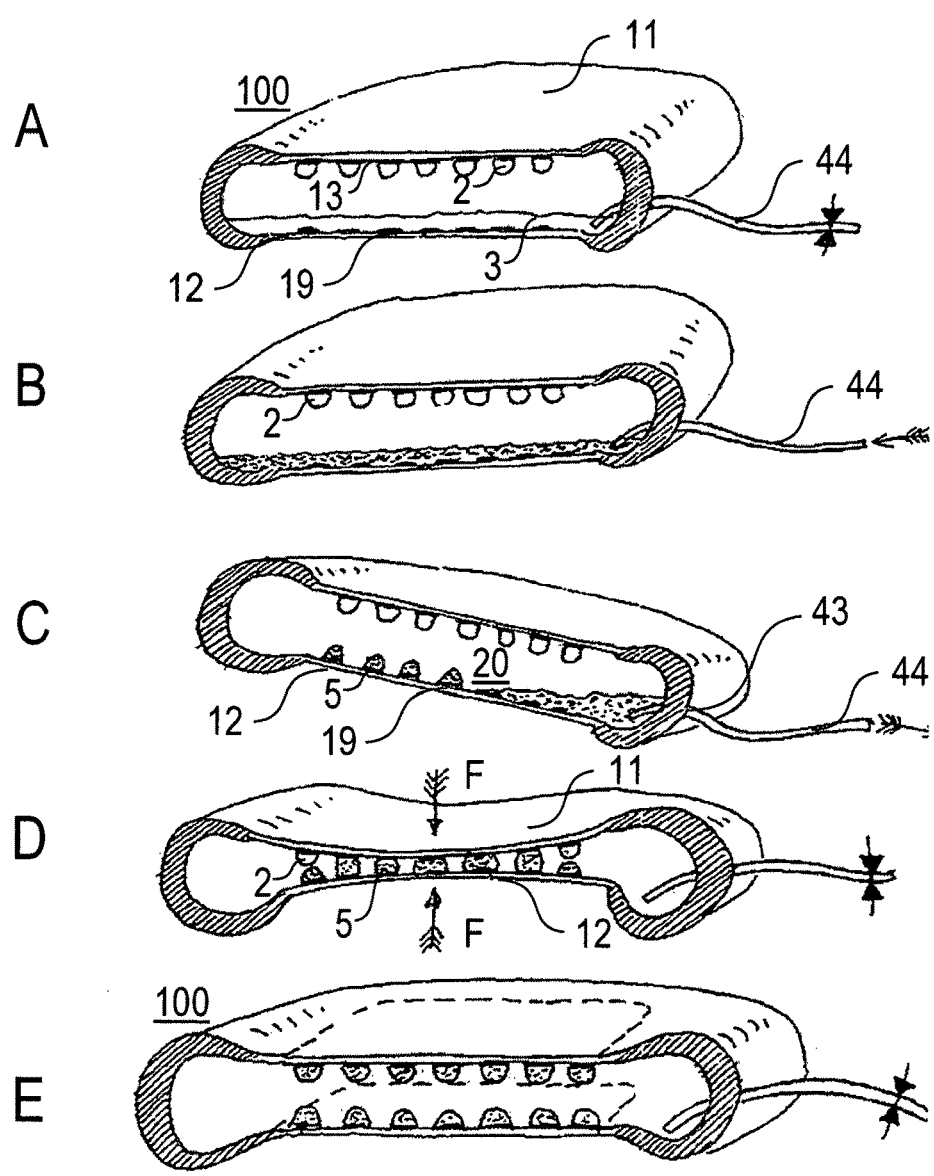
FIGS. 13A to 13E a schematic illustration of a further embodiment of the method according to the invention.

FIG. 13 illustrates, by way of example, a method sequence for cryopreservation of cells in hanging droplets. The cryopreservation takes place, for example, following culturing in the hanging droplets in order to store permanently the cells obtained. A culture vessel 100 is used which is essentially constructed as shown in FIG. 2. In addition, the culture vessel 100 has hydrophilic surface regions 19 on the inside of the bottom section 12 which are separated from one another by hydrophobic surface regions. The hydrophilic surface regions 19 are positioned matching the geometric arrangement of the holding elements 14 on the culturing area 13 on the cover section 11.

FIG. 13A shows the culture vessel 100 in the unfolded state in which the hanging droplets 2 are arranged on the culturing area 13 and the bottom section 12 is covered with a liquid 3. In order to prepare the cryopreservation of the droplets 2, a cryoprotectant, for example DMSO, is added via the tube 44 to the liquid 3 or the liquid 3 is replaced with a solution of a cryoprotectant (FIG. 13B). Subsequently, the culture vessel 100 is tilted so that the liquid in the inner space 20 flows to the media interface 43 and can flow away via the tube 44. Herein, droplets 5 with the cryoprotectant remain on the hydrophilic surface regions 19 of the bottom section 12 (FIG. 13C).

Subsequently, the culture vessel 100 is brought into the compressed state (FIG. 13D). The cover and bottom sections 11, 12 are brought together under the influence of external forces F until the droplets 2 in which the biological cells have been cultured and the droplets 5 blend together. Since the droplets 2, 5 lie exactly opposite one another and the lateral spacings between the droplets are sufficiently large, the cells remain in the droplets at reproducible positions.

The cryopreservation can take place in the compressed state (FIG. 13D) or in the subsequent unfolded-again state (FIG. 13E) of the culture vessel 100. For this purpose, the culture vessel 100 is brought into surroundings at a reduced temperature, for example, in liquid nitrogen or in the cold vapor over liquid nitrogen in a nitrogen tank. In the frozen state, the wall regions which carry the droplets can be separated from the remaining parts of the culture vessel 100.

The vessel wall of the culture vessel 100 according to the invention can be provided with thermally conductive elements, for example, a metal coating in order to accelerate the cooling when the coolant is applied. Furthermore, the culture vessel 100 can be provided with heating elements, for example, resistive heating elements which are integrated into the vessel wall. The heating elements can support rapid and even thawing following ending of the cooling preservation.

Figure 14:
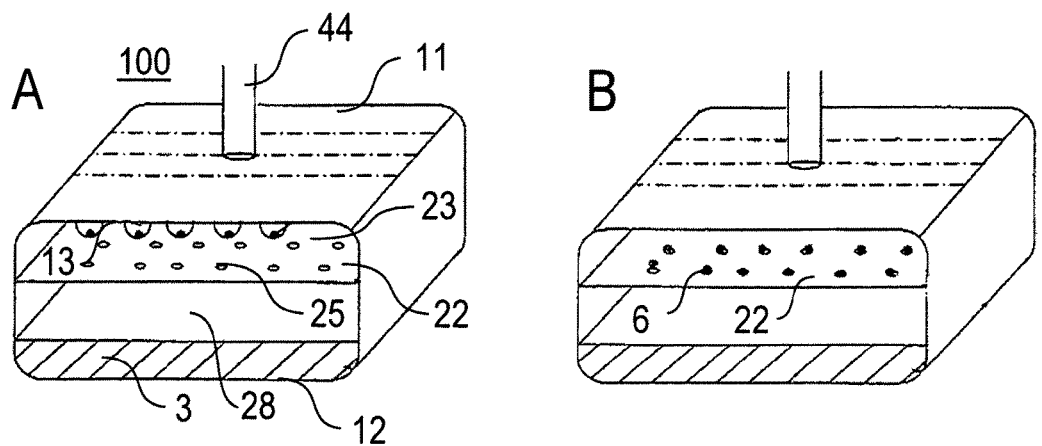
FIGS. 14A and 14B a schematic illustration of further variants of the method according to the invention.

FIG. 14 shows a further variant of a culture vessel 100 according to the invention, the inner space 20 of which is divided by an intermediate wall 22 into an upper (23) and a lower (28) horizontal chamber. The intermediate wall 22 is a plastics film which has pores 25 of a defined size (>100 μm).

The formation of the hanging droplets 2 and their culturing takes place as described above. In the compressed state of the culture vessel 100, the liquid 3 from the bottom section 12 penetrates the intermediate wall 22 so that the culturing area 13 is wetted and the hanging droplets 2 are collected on the holding elements. During harvesting of the cultured cells, the task can be to separate cell aggregates from individual cells. For this purpose, a culture medium or a buffer solution is fed in via the tube 44 in order to flush the hanging droplets 2 off the culturing area 13. The liquid and the individual cells can pass through the pores in the intermediate wall 22, whereas the cell aggregates 6 are immobilized on the intermediate wall 22 (FIG. 14B). Subsequently, the intermediate wall 22 can be released from the culture vessel 100 at pre-determined breaking sites in order to pass the collected cell aggregates on for further investigations.

Figure 15:
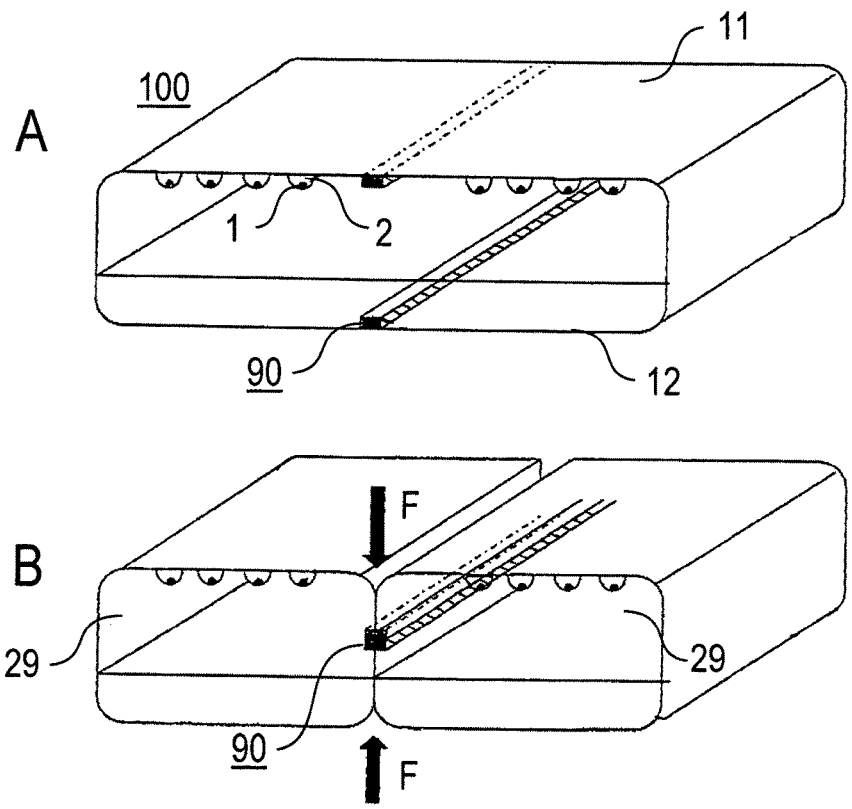
FIGS. 15A and 15B schematic illustrations of further embodiments of the culture vessel according to the invention which is provided with coupling elements for forming vertical chambers.

FIG. 15 shows a further embodiment of the culture vessel 100 according to the invention wherein the cover and bottom sections 11, 12 are provided with line-shaped coupling elements 90. The coupling elements 90 comprise composite materials such as polyethylene, polypropylene on the internal sides of the cover and bottom sections 11, 12, which are bound to one another as a reaction to an external pressure. The use of the culture vessel 100 of FIG. 15 takes place in that initially the hanging droplets 2 with the biological cells 1 are formed as described above. If, following a particular culturing duration, part of the culture vessel 100 is to be separated off, for example, in order to carry out cryopreservation or further differentiation or to undertake separate storage, external forces F are applied to the coupling elements 90 (FIG. 15B) so that the coupling elements 90 fuse with one another. In this way, two vertical chambers 29 are formed which can be separated from one another.

In the variant of the culture vessel according to the invention shown in FIGS. 16 to 20, the holding elements 14 comprise hydrophilic step elements in the form of circumferential rings 14.1 which are positioned on the culturing area 13 and which each enclose a hydrophilic surface portion 14.2 of the culturing area 13. The rings 14.1 are manufactured from plastics with a height of, for example, 500 μm to 1 mm and a diameter of, for example, 5 to 20 mm. The vessel wall of the culture vessel 100 is provided with a rotary mounting 60 and a tube 44 in the region of the side section 15. The rotary mounting 60 comprises two laterally projecting posts 61 with which the culture vessel 100 can be suspended in a carrier (not shown) and can be rotated. Media can be fed via the tube 44 into the inner space of the culture vessel 100, particularly into the bottom section 12.

Figure 16:
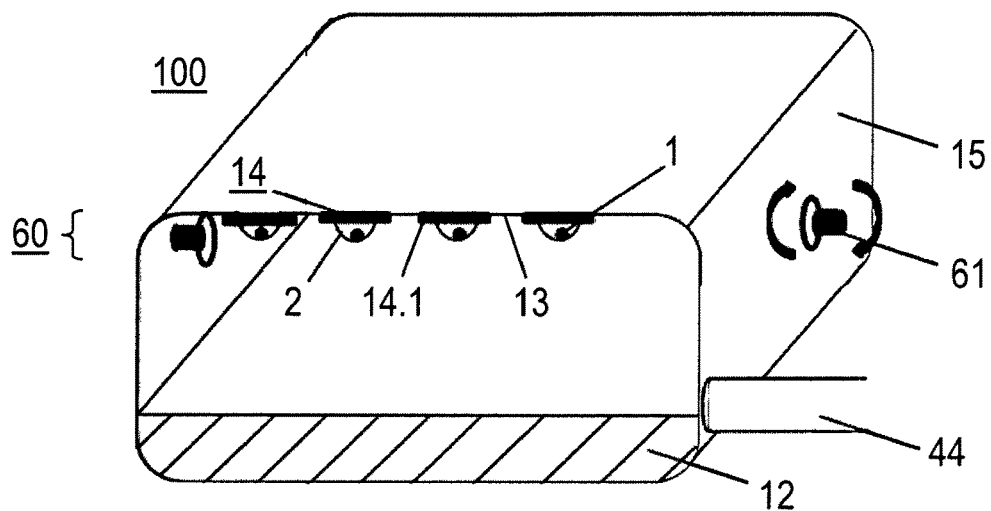
FIGS. 16 to 20 schematic illustrations of further embodiments of the culture vessel according to the invention which is provided with coupling elements for forming vertical chambers.
Figure 17:
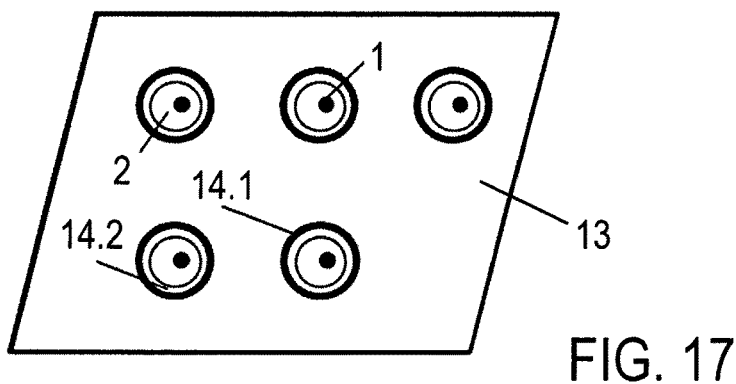

Culturing in the culture vessel 100 of FIG. 16 takes place in that initially the holding elements 14 are each loaded with hanging droplets 2 with cells, as described above. As a result of the culturing, the cells multiply to cell aggregates 1. A plan view of a portion of the culturing area 13 is shown in FIG. 17. The droplets 2 with the cell aggregates 1 are positioned in the hydrophilic surface portions 14.2 which are delimited by the rings 14.1. The hydrophilic surface portions 14.2 can also be occupied by specific, for example, fluorescence-marked antibodies (see FIG. 19).

Figure 18:
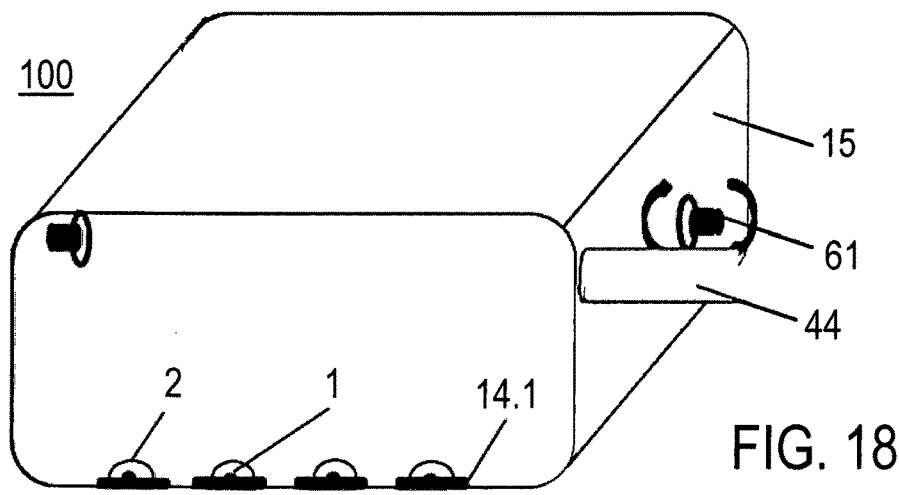

For further adherent culturing, the liquid is drawn off from the bottom section 12 of the culture vessel 100 via the tube 44. Subsequently, the culture vessel 100 is rotated through 180° with the aid of the rotary mounting 60, as shown in FIG. 18. Now the cell aggregates 1 settle and can adhere within the areas on the culturing area delimited by the rings 14.1.

Following adhesion, culture medium can be poured in via the tube 44 so that subsequent adherent culturing of the cell aggregates 1 in the droplets 2 is possible.

Figure 19:
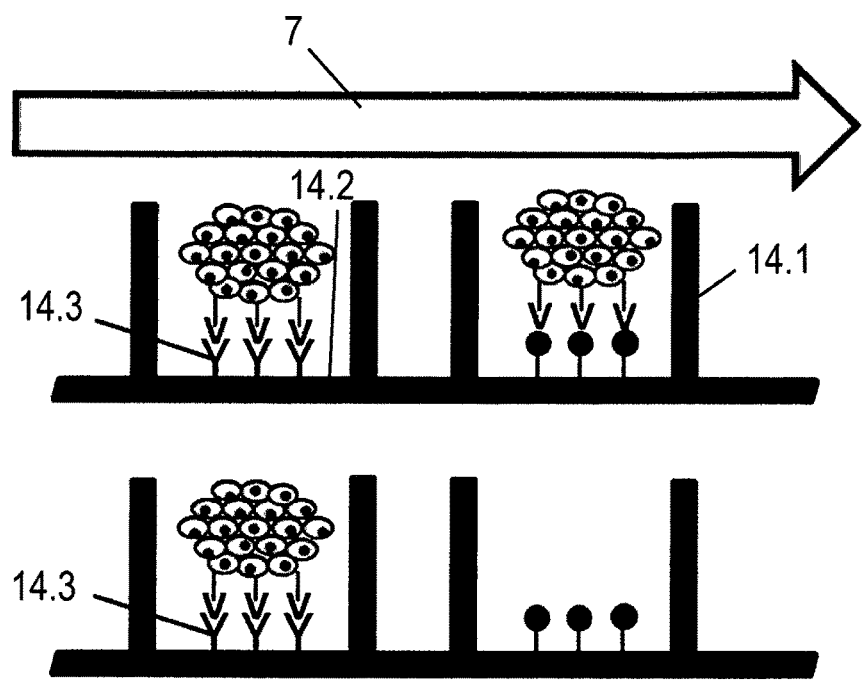
Figure 20:
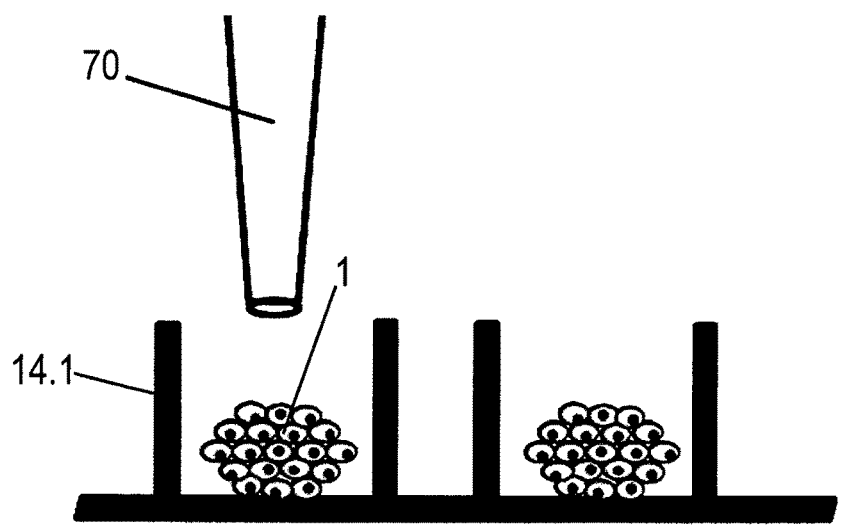

If the surface portions 14.2 are occupied by specific antibodies 14.3, an antigen-antibody binding with the cell aggregates 1 takes place (FIG. 19). This can be used, firstly, for cell separation in that the unbound cell aggregates are flushed away with a liquid stream 7 by means of the tube (see FIG. 19, bottom right). If the antibodies are additionally provided with fluorescence markers, detection of specific cells can take place in the culture vessel, for example, by means of a fluorescence measurement. Furthermore, the cell aggregates 1 which are present spatially separated from one another within the rings 14.1 in their own cavities, can be used for screening in that different substances are added to the cavities manually or automatically with the aid of a pipette 70 (FIG. 20).

The features of the invention disclosed in the above description, the drawings and the claims can be significant either individually or in combination for the realization of the invention in its various embodiments.

The invention claimed is:

1. A cultivation vessel, which is configured for culturing biological cells in hanging droplets, comprising:
   a vessel wall which has a cover section and a bottom section, wherein
   the cover section is configured for providing a culturing area and the bottom section is configured for receiving a liquid,
   the vessel wall encloses an inner space of the cultivation vessel on all sides,
   the culturing area has holding elements which are configured for positioning the droplets, wherein the culturing area is able to accommodate the droplets hanging freely in the inner space,
   the holding elements comprise hydrophilic surface regions of the culturing area which are separated from one another by hydrophobic surface regions,
   the vessel wall is movable so that the holding elements can be wetted with the liquid from the bottom section, and
   the vessel wall is deformable and the cover section and the bottom section are movable relative to one another so that a distance between the cover section and the bottom section can be reduced and the holding elements can approach the bottom section.

2. The cultivation vessel according to claim 1, wherein the hydrophilic surface regions have at least one of the features:
   the hydrophilic surface regions form a regular pattern,
   the hydrophilic surface regions are formed by a surface functionalization of the culturing area, and
   the hydrophilic surface regions are formed by step elements on the culturing area.

3. The cultivation vessel according to claim 1, wherein:
   the vessel wall comprises a flexible film material, wherein the distance between the cover and bottom sections is adjustable by at least one of an effect of an internal pressure in the cultivation vessel and a foldable inner carrier.

4. The cultivation vessel according to claim 1, wherein:
   the vessel wall is made partially from an elastically deformable material, wherein the distance between the cover and bottom sections is adjustable under an effect of an elastic restoring force of the elastically deformable material.

5. The cultivation vessel according to claim 1, wherein:
   the vessel wall has a side section comprising an elastically deformable material, by way of which the cover section and the bottom section are connected to one another.

6. The cultivation vessel according to claim 1, wherein:
   the bottom section has a bottom area opposite to the culturing area with a plurality of hydrophilic surface regions which are separated from one another by hydrophobic surface regions and are arranged matching positions of the hydrophilic surface regions of the culturing area.

7. The cultivation vessel according to claim 1, wherein:
   the culturing area is formed directly by an inner surface of the cover section.

8. The cultivation vessel according to claim 1, which further comprises
   at least one intermediate wall dividing the inner space into two horizontal chambers.

9. The cultivation vessel according to claim 8, wherein the at least one intermediate wall has at least one of the properties:

the at least one intermediate wall is manufactured from a material which allows molecular diffusion, the at least one intermediate wall has pores, the at least one intermediate wall has pre-determined breaking sites, and the at least one intermediate wall is restricted to a subregion of the inner space.

10. The cultivation vessel according to claim 8, wherein:

the at least one intermediate wall is part of the cover section and the culturing area is formed by a surface of the at least one intermediate wall facing toward the bottom section, or the at least one intermediate wall is part of the bottom section.

11. The cultivation vessel according to claim 1, which further comprises:

a carrier device which supports the cultivation vessel at an underside of said cultivation vessel.

12. The cultivation vessel according to claim 11, wherein:

the carrier device has mass elements with which a mass center of gravity of the cultivation vessel is formed in the bottom section or adjacent thereto.

13. The cultivation vessel according to claim 1, which further comprises:

a media device having at least one closable media interface configured for at least one of a supply and a removal of at least one of liquid and gaseous media into and out of the inner space.

14. The cultivation vessel according to claim 1, wherein:

the vessel wall has at least one window section which is configured for at least one of an optical observation and an invasive penetration by a tool.

15. The cultivation vessel according to claim 14, wherein:

the at least one window section comprises a planar region of the cover section which comprises an optically transparent material.

16. The cultivation vessel according to claim 1, which further comprises at least one of:

an outer receptacle device for receiving the vessel wall and a transparent plate against which the cover section lies if the distance between the cover section and the bottom section is adjusted, and an outer clamping device with which a volume of the inner space is adjustable.

17. The cultivation vessel according to claim 1, wherein:

the cover section and the bottom section have line-shaped coupling elements at which the cover section and the bottom section can be connected to one another so that the inner space is divided into vertical chambers.

18. A method for culturing biological cells in hanging droplets in a cultivation vessel according to claim 1, comprising the steps:

providing a suspension, which contains the biological cells at the bottom section of the cultivation vessel, wetting the culturing area with a suspension and forming hanging droplets at the culturing area, and culturing the biological cells in the hanging droplets.

19. The method according to claim 18, wherein the wetting of the culturing area comprises the steps:

compressing the cultivation vessel such that the distance between the cover section and the bottom section is reduced and the culturing area touches the suspension, and restoring the vessel wall such that the distance between the cover section and the bottom section is increased and the freely hanging droplets of the suspension are formed on the holding elements of the culturing area.

20. The method according to claim 19, wherein the compression and restoration of the vessel wall comprises at least one of:

an adjustment of an internal pressure in the cultivation vessel, actuating a foldable inner carrier in the cultivation vessel, and a deformation under the effect of an elastic restoring force of the material of the vessel wall.

21. The method according to claim 18, further comprising the steps:

supply and removal of at least one of liquid and gaseous media into and out of the inner space.

22. The method according to claim 18, further comprising at least one of the steps:

optical observation of the hanging droplets through at least one window section in the vessel wall, and invasive penetration of at least one window section in the vessel wall with a tool and access to the hanging droplets.

23. The method according to claim 18, further comprising at least one of the steps:

subdividing the inner space of the cultivation vessel into horizontal chambers, and subdividing the inner space of the cultivation vessel into vertical chambers.

* * * * *